US011724003B2

(12) United States Patent
Strbac

(10) Patent No.: US 11,724,003 B2
(45) Date of Patent: Aug. 15, 2023

(54) FIREARM TRIGGER MECHANISM

(71) Applicant: ABC IP, LLC, Dover, DE (US)

(72) Inventor: Mladen Thomas Strbac, Cleveland, OH (US)

(73) Assignee: ABC IP, LLC, Dover, DE (US)

( * ) Notice: Subject to any disclaimer, the term of this patent is extended or adjusted under 35 U.S.C. 154(b) by 0 days.

(21) Appl. No.: 18/048,572

(22) Filed: Oct. 21, 2022

(65) Prior Publication Data

US 2023/0221087 A1    Jul. 13, 2023

Related U.S. Application Data

(60) Provisional application No. 63/297,884, filed on Jan. 10, 2022.

(51) Int. Cl.
*F41A 19/24*     (2006.01)
*F41A 19/10*     (2006.01)
(Continued)

(52) U.S. Cl.
CPC .............. *F41A 19/10* (2013.01); *F41A 17/48* (2013.01); *F41A 19/15* (2013.01); *F41A 19/24* (2013.01)

(58) Field of Classification Search
CPC .......... F41A 19/24; F41A 19/10; F41A 19/15; F41A 19/16; F41A 17/46
See application file for complete search history.

(56) References Cited

U.S. PATENT DOCUMENTS 2,765,562 A    10/1956   Rober et al.
3,045,555 A     7/1962   Stoner
(Continued)

FOREIGN PATENT DOCUMENTS

DE        582963 C     8/1933
DE     4008351 A1     9/1991
(Continued)

OTHER PUBLICATIONS

Statutory Invention Registration No. H107, Inventor: Bauer, Published Aug. 5, 1986 (8 pages).

*Primary Examiner* — J. Woodrow Eldred
(74) *Attorney, Agent, or Firm* — Wood Herron & Evans LLP

(57) ABSTRACT

A trigger mechanism that can be used in AR-pattern firearms has a hammer, a trigger member, a disconnector, a locking member, and a "three position" safety selector having safe, standard semi-automatic, and forced reset semi-automatic positions. In the standard semi-automatic position, rearward movement of the bolt carrier causes rearward pivoting of the hammer such that the disconnector hook catches the hammer hook, at which time a user must manually release the trigger member to free the hammer from the disconnector to permit the hammer and trigger member to pivot to the set positions so that the user can pull the trigger member to fire the firearm. In the forced reset semi-automatic position, rearward movement of the bolt carrier causes rearward pivoting of the hammer causing the trigger member to be forced to the set position, the safety selector preventing the disconnector hook from catching the hammer hook, and thereafter when the bolt carrier reaches the substantially in-battery position the user can pull the trigger member to fire the firearm without manually releasing the trigger member. The locking member is pivotable between a first position at which the locking member mechanically blocks the trigger member from moving to the released position and a second position at which the locking member does not mechanically block the trigger member allowing the trigger member to be moved to the released position. The locking member is spring biased toward the first position and moved against the spring bias to the second position by contact from the bolt (Continued)

carrier during forward movement of the bolt carrier as the bolt carrier reaches a substantially in-battery position.

14 Claims, 18 Drawing Sheets

(51) Int. Cl.
*F41A 17/48* (2006.01)
*F41A 19/15* (2006.01)

(56) References Cited

U.S. PATENT DOCUMENTS

| | | |
|---|---|---|
| 3,292,492 A | 12/1966 | Sturtevant |
| 3,301,133 A | 1/1967 | Sturtevant |
| 3,670,442 A | 6/1972 | Kennedy et al. |
| 4,023,465 A | 5/1977 | Inskip |
| 4,057,003 A | 11/1977 | Atchisson |
| 4,151,670 A | 5/1979 | Rath |
| 4,276,808 A | 7/1981 | York |
| 4,433,610 A | 2/1984 | Tatro |
| 4,463,654 A | 8/1984 | Barnes et al. |
| 4,516,466 A | 5/1985 | Jennie |
| 4,580,484 A | 4/1986 | Moore |
| 4,656,993 A | 4/1987 | Yuzawa et al. |
| 4,658,702 A | 4/1987 | Tatro |
| 4,693,170 A | 9/1987 | Atchisson |
| 4,697,495 A | 10/1987 | Beretta |
| 4,787,288 A | 11/1988 | Miller |
| 4,937,964 A | 7/1990 | Crandall |
| 5,149,898 A | 9/1992 | Chesnut et al. |
| 5,183,959 A | 2/1993 | McCoan et al. |
| 5,223,649 A | 6/1993 | Claridge |
| 5,339,721 A | 8/1994 | Beretta |
| 5,517,897 A | 5/1996 | Perrine |
| 5,614,691 A | 3/1997 | Taylor |
| 5,623,114 A | 4/1997 | Soper |
| 5,682,699 A | 11/1997 | Gentry |
| 5,701,698 A | 12/1997 | Wesp et al. |
| 5,704,153 A | 1/1998 | Kaminski et al. |
| 5,760,328 A | 6/1998 | Robbins |
| 5,770,814 A | 6/1998 | Ealovega |
| 6,101,918 A | 8/2000 | Akins |
| 6,360,467 B1 | 3/2002 | Knight |
| 6,601,331 B2 | 8/2003 | Salvitti |
| 6,718,680 B2 | 4/2004 | Roca et al. |
| 6,722,072 B1 | 4/2004 | McCormick |
| 6,851,346 B1 | 2/2005 | Herring |
| 6,889,459 B1 | 5/2005 | Salvitti |
| 6,976,416 B2 | 12/2005 | Ealovega |
| 7,051,638 B2 | 5/2006 | Thomele |
| 7,162,824 B1 | 1/2007 | McCormick |
| 7,213,359 B2 | 5/2007 | Beretta |
| 7,293,385 B2 | 11/2007 | McCormick |
| 7,337,574 B2 | 3/2008 | Crandall et al. |
| 7,347,021 B1 | 3/2008 | Jones |
| 7,398,723 B1 | 7/2008 | Blakley |
| 7,421,937 B1 | 9/2008 | Gangl |
| 7,634,959 B2 | 12/2009 | Frickey |
| 7,661,220 B2 | 2/2010 | Crandall et al. |
| 7,806,039 B1 | 10/2010 | Gomez |
| 8,037,805 B1 | 10/2011 | Neroni |
| 8,112,928 B2 | 2/2012 | Keough |
| 8,127,658 B1 | 3/2012 | Cottle |
| 8,156,854 B2 | 4/2012 | Brown |
| 8,443,537 B2 | 5/2013 | Curry |
| 8,464,454 B2 | 6/2013 | Martin et al. |
| 8,490,309 B2 | 7/2013 | Zukowski |
| 8,667,881 B1 | 3/2014 | Hawbaker |
| 8,695,477 B2 | 4/2014 | Esch |
| 8,720,096 B2 | 5/2014 | Siddle |
| 8,820,211 B1 | 9/2014 | Hawbaker |
| 8,893,607 B2 | 11/2014 | Audibert et al. |
| 8,925,234 B1 | 1/2015 | Barrett |
| 8,985,006 B1 | 3/2015 | Christensen et al. |
| 9,016,187 B2 | 4/2015 | Findlay |
| 9,021,732 B2 | 5/2015 | Johnson |
| 9,021,733 B1 | 5/2015 | DiChario |
| 9,052,150 B2 | 6/2015 | Talasco |
| 9,121,661 B2 | 9/2015 | Calvete |
| 9,146,066 B1 | 9/2015 | Cason |
| 9,146,067 B2 | 9/2015 | Stakes |
| 9,182,189 B2 | 11/2015 | Seigler |
| 9,228,786 B2 | 1/2016 | Sullivan et al. |
| 9,310,150 B1 | 4/2016 | Geissele |
| 9,347,726 B1 | 5/2016 | Thomas |
| 9,448,023 B2 | 9/2016 | Sheets, Jr. et al. |
| 9,476,660 B2 | 10/2016 | Potter et al. |
| 9,513,076 B2 | 12/2016 | Kolev et al. |
| 9,568,264 B2 | 2/2017 | Graves |
| 9,618,288 B2 | 4/2017 | Wilson |
| 9,618,289 B1 | 4/2017 | Geissele |
| 9,625,231 B1 | 4/2017 | Hass |
| 9,631,886 B2 | 4/2017 | Findlay |
| 9,651,329 B2 | 5/2017 | Hittmann |
| 9,658,007 B2 | 5/2017 | Withey |
| 9,683,800 B2 | 6/2017 | Sewell, Jr. et al. |
| 9,733,031 B1 | 8/2017 | Sylvester et al. |
| 9,759,504 B2 | 9/2017 | Geissele |
| 9,777,980 B2 | 10/2017 | Heizer |
| 9,810,493 B2 | 11/2017 | Fluhr et al. |
| 9,810,496 B2 | 11/2017 | Kolev et al. |
| 9,816,772 B2 | 11/2017 | Graves |
| 9,829,263 B2 | 11/2017 | Bonner |
| 9,835,398 B2 | 12/2017 | Biegel |
| 9,863,730 B2 | 1/2018 | Elftmann |
| 9,869,522 B2 | 1/2018 | Larson, Jr. et al. |
| 9,874,417 B2 | 1/2018 | Zajk et al. |
| 9,927,197 B1 | 3/2018 | Geissele |
| 9,939,221 B2 | 4/2018 | Graves |
| 10,002,500 B2 | 6/2018 | Hall et al. |
| 10,006,734 B1 | 6/2018 | Findlay |
| 10,030,924 B1 | 7/2018 | Smith |
| 10,077,960 B2 | 9/2018 | Geissele |
| 10,107,580 B2 | 10/2018 | Fellows et al. |
| 10,254,067 B2 | 4/2019 | Foster |
| 10,267,584 B2 | 4/2019 | Kasanjian-King |
| 10,330,413 B2 | 6/2019 | Williams et al. |
| 10,488,136 B2 | 11/2019 | Sullivan et al. |
| 10,502,511 B2 | 12/2019 | Graves |
| 10,514,223 B1 | 12/2019 | Rounds |
| 10,584,932 B2 | 3/2020 | Foster |
| 10,816,297 B1 * | 10/2020 | Williams ............... F41A 19/46 |
| 11,287,205 B2 | 3/2022 | Biegel |
| 11,293,715 B1 | 4/2022 | Newsome et al. |
| 11,346,627 B1 | 5/2022 | DeMonico |
| 2006/0048426 A1 | 3/2006 | Crandall |
| 2006/0101695 A1 | 5/2006 | Longueira |
| 2007/0051236 A1 | 3/2007 | Groves et al. |
| 2007/0199435 A1 | 8/2007 | Hochstrate et al. |
| 2009/0151213 A1 | 6/2009 | Bell |
| 2009/0188145 A1 | 7/2009 | Fluhr et al. |
| 2011/0209607 A1 | 9/2011 | St. George |
| 2013/0118343 A1 | 5/2013 | Hirt |
| 2014/0311004 A1 | 10/2014 | Barrett |
| 2016/0010933 A1 | 1/2016 | Bonner |
| 2016/0102933 A1 | 4/2016 | Graves |
| 2016/0161202 A1 | 6/2016 | Larue |
| 2017/0176124 A1 | 6/2017 | Wilson |
| 2017/0219307 A1 | 8/2017 | Foster |
| 2017/0276447 A1 | 9/2017 | Foster |
| 2017/0284761 A1 | 10/2017 | Lewis et al. |
| 2017/0299309 A1 | 10/2017 | Fellows et al. |
| 2017/0328663 A1 | 11/2017 | Fellows et al. |
| 2018/0066911 A1 | 3/2018 | Graves |
| 2018/0087860 A1 | 3/2018 | Sullivan et al. |
| 2018/0112944 A1 | 4/2018 | Underwood et al. |
| 2018/0195823 A1 | 7/2018 | Schafer et al. |
| 2018/0202740 A1 | 7/2018 | Elftmann, Jr. |
| 2018/0231342 A1 | 8/2018 | Martinez |
| 2020/0191513 A1 * | 6/2020 | Foster ............... F41A 19/16 |
| 2021/0222974 A1 | 7/2021 | Graves |
| 2022/0364812 A1 * | 11/2022 | Fellows ............... F41A 19/24 |

(56) References Cited

U.S. PATENT DOCUMENTS

FOREIGN PATENT DOCUMENTS

| | | |
|---|---:|---|
| EP | 1678458 B1 | 2/2012 |
| EP | 2950033 B1 | 11/2016 |
| TW | 409847 U | 10/2000 |
| WO | 2016/028337 A1 | 2/2016 |
| WO | 2018/058174 A1 | 4/2018 |

* cited by examiner

FIREARM TRIGGER MECHANISM

RELATED APPLICATIONS

This application claims the priority benefit of US Provisional Patent Application No. 63/297,884 filed Jan. 10, 2022, which is hereby incorporated by reference herein as if fully set forth in its entirety.

TECHNICAL FIELD

The present invention relates generally to a firearm trigger mechanism, and more particularly to a semiautomatic trigger that is selectively mechanically reset by movement of the bolt carrier.

BACKGROUND

In a standard semiautomatic firearm, actuation of the trigger releases a sear, allowing a hammer or striker to fire a chambered ammunition cartridge. Part of the ammunition's propellant force is used to cycle the action, extracting and ejecting a spent cartridge and replacing it with a loaded cartridge. The cycle includes longitudinal reciprocation of a bolt and/or carrier, which also resets the hammer or striker.

A standard semiautomatic trigger mechanism includes a disconnector, which holds the hammer or striker in a cocked position until the trigger member is reset to engage the sear. This allows the firearm to be fired only a single time when the trigger is pulled and held, because the user is not typically able to release the trigger rapidly enough so that the sear engages before the bolt or bolt carrier returns to its in-battery position. The disconnector prevents the firearm from either firing multiple rounds on a single pull of the trigger, or from allowing the hammer or striker to simply "follow" the bolt as it returns to battery without firing a second round, but leaving the hammer or striker uncocked.

For various reasons, shooters desire to increase the rate of semiautomatic fire. Sometimes this is simply for entertainment and the feeling of shooting a machine gun. In the past, users have been known to employ "bump firing" to achieve rapid semiautomatic fire. Bump firing uses the recoil of the semiautomatic firearm to fire shots in rapid succession. The process involves bracing the rifle with the non-trigger hand, loosening the grip of the trigger hand (but leaving the trigger finger in its normal position in front of the trigger), and pushing the rifle forward in order to apply pressure on the trigger from the finger while keeping the trigger finger stationary. When fired with the trigger finger held stationary, the firearm will recoil to the rear and allow the trigger to reset as it normally does. When the non-trigger hand pulls the firearm away from the body and back forward toward the original position, it causes the trigger to be pressed against the stationary finger again, firing another round as the trigger is pushed back.

Devices for increasing the rate of semiautomatic fire are shown in U.S. Pat. Nos. 9,568,264; 9,816,772; and 9,939,221, issued to Thomas Allen Graves. The devices shown in these patents forcefully reset the trigger with rigid mechanical contact between the trigger member and the bolt as the action cycles. To adapt this invention to an AR-pattern firearm, for example, would require not only a modified fire control mechanism, but also a modified bolt carrier.

Other devices for increasing the rate of semiautomatic fire are shown in U.S. Pat. Nos. 10,514,223 and 11,346,627, which are hereby incorporated by reference herein as if fully set forth in their entirety. In these devices the hammer forces the trigger to the set position, and a locking bar prevents early hammer release.

Another device for increasing the rate of semiautomatic fire is shown in U.S. Pat. No. 7,398,723, issued to Brian A. Blakley, and is hereby incorporated by reference herein as if fully set forth in its entirety. The device shown in this patent has a pivoting cam which is contacted by the rearwardly traveling bolt carrier, pivoting the cam rearwardly such that the bottom surface of the cam presses downward on the trigger-extension, forcing the rear of the trigger down, and thereby moving forward the surface of the trigger that an operator's finger engages. Another device for increasing the rate of semiautomatic fire employing a pivoting cam arrangement is shown in U.S. Provisional Patent Application No. 63/374,941 filed Sep. 8, 2022, also invented by Brian A. Blakley, and which is hereby incorporated by reference herein as if fully set forth in its entirety. This pivoting cam arrangement incorporates a three-position safety selector and associated structure to provide safe, standard semi-automatic, and forced reset semi-automatic modes.

Further improvement in forced reset triggers is desired.

SUMMARY OF INVENTION

The present invention provides a semiautomatic trigger mechanism for increasing rate of fire that can be retrofitted into popular existing firearm platforms. In particular, this invention provides a trigger mechanism that can be used in AR-pattern firearms with an otherwise standard M16-pattern bolt carrier assembly. The present invention is particularly adaptable for construction as a "drop-in" replacement trigger module that only requires insertion of two assembly pins and the safety selector. Advantageously, the present invention provides a "three position" trigger mechanism having safe, standard semi-automatic, and forced reset semi-automatic positions.

In one aspect, a firearm trigger mechanism comprises a hammer having a sear catch and a hook for engaging a disconnector and adapted to be mounted in a fire control mechanism pocket of a receiver to pivot on a transverse hammer pivot axis between set and released positions, the hammer adapted to be pivoted rearward by rearward movement of a bolt carrier, a trigger member having a sear and adapted to be mounted in the fire control mechanism pocket to pivot on a transverse trigger member pivot axis between set and released positions, the trigger member having a surface positioned to be contacted by the hammer during rearward pivoting of the hammer to cause the trigger member to be forced to the set position, wherein the sear and sear catch are in engagement in the set positions of the hammer and trigger member and are out of engagement in the released positions of the hammer and trigger member, a disconnector having a hook for engaging the hammer and adapted to be mounted in the fire control mechanism pocket to pivot on the transverse trigger member pivot axis, a locking member adapted to be mounted in the fire control mechanism pocket to pivot on a transverse locking member pivot axis, the locking member being pivotable between a first position at which the locking member mechanically blocks the trigger member from moving to the released position and a second position at which the locking member does not mechanically block the trigger member allowing the trigger member to be moved to the released position, the locking member spring biased toward the first position and adapted to be moved against the spring bias to the second position by contact from the bolt carrier during forward movement of the bolt carrier as the bolt carrier reaches a substantially in-battery position, and a safety selector adapted to be mounted in the fire control mechanism pocket to pivot between safe, standard semi-automatic, and forced reset semi-automatic positions. In the standard semi-automatic position, rearward movement of the bolt carrier causes rearward pivoting of the hammer such that the disconnector hook catches the hammer hook, at which time a user must manually release the trigger member to free the hammer from the disconnector to permit the hammer and trigger member to pivot to the set positions so that the user can pull the trigger member to fire the firearm. In the forced reset semi-automatic position, rearward movement of the bolt carrier causes rearward pivoting of the hammer causing the trigger member to be forced to the set position, the safety selector preventing the disconnector hook from catching the hammer hook, and thereafter when the bolt carrier reaches the substantially in-battery position the user can pull the trigger member to fire the firearm without manually releasing the trigger member.

The safety selector can have a protuberance thereon which, when the safety selector is in the forced reset semi-automatic position, contacts the disconnector preventing the disconnector hook from catching the hammer hook. The trigger mechanism can further include a spring which biases the trigger member towards the set position.

In another aspect, a firearm trigger mechanism comprises a housing having a first pair of transversely aligned openings for receiving a hammer pin and a second pair of transversely aligned openings for receiving a trigger member pin, a hammer having a sear catch and a hook for engaging a disconnector and mounted in the housing to pivot on the hammer pin between set and released positions, the hammer adapted to be pivoted rearward by rearward movement of a bolt carrier, a trigger member having a sear and mounted in the housing to pivot on the trigger member pin between set and released positions, the trigger member having a surface positioned to be contacted by the hammer during rearward pivoting of the hammer to cause the trigger member to be forced to the set position, wherein the sear and sear catch are in engagement in the set positions of the hammer and trigger member and are out of engagement in the released positions of the hammer and trigger member, a disconnector having a hook for engaging the hammer and mounted in the housing to pivot on the trigger member pin, a locking member mounted in the housing to pivot on a transverse locking member pin, the locking member being pivotable between a first position at which the locking member mechanically blocks the trigger member from moving to the released position and a second position at which the locking member does not mechanically block the trigger member allowing the trigger member to be moved to the released position, the locking member spring biased toward the first position and adapted to be moved against the spring bias to the second position by contact from the bolt carrier during forward movement of the bolt carrier as the bolt carrier reaches a substantially in-battery position, and a safety selector adapted to be mounted in a fire control mechanism pocket of a receiver to pivot between safe, standard semi-automatic, and forced reset semi-automatic positions. In the standard semi-automatic position, rearward movement of the bolt carrier causes rearward pivoting of the hammer such that the disconnector hook catches the hammer hook, at which time a user must manually release the trigger member to free the hammer from the disconnector to permit the hammer and trigger member to pivot to the set positions so that the user can pull the trigger member to fire the firearm. In the forced reset semi-automatic position, rearward movement of the bolt carrier causes rearward pivoting of the hammer causing the trigger member to be forced to the set position, the safety selector preventing the disconnector hook from catching the hammer hook, and thereafter when the bolt carrier reaches the substantially in-battery position the user can pull the trigger member to fire the firearm without manually releasing the trigger member.

The safety selector can have a protuberance thereon which, when the safety selector is in the forced reset semi-automatic position, contacts the disconnector preventing the disconnector hook from catching the hammer hook. The transversely aligned pairs of openings in the housing for receiving the hammer and trigger member pins can be adapted to be aligned with assembly pin openings in the fire control mechanism pocket. The trigger mechanism can further include a spring which biases the trigger member towards the set position. The spring can be a compression spring positioned between a forward end of the trigger member and a floor of the housing.

In another aspect, a firearm comprises a receiver having a fire control mechanism pocket therein, a reciprocating bolt carrier, a hammer having a sear catch and a hook for engaging a disconnector and mounted in the fire control mechanism pocket to pivot on a transverse hammer pivot axis between set and released positions, the hammer pivoted rearward by rearward movement of the bolt carrier, a trigger member having a sear and mounted in the fire control mechanism pocket to pivot on a transverse trigger member pivot axis between set and released positions, the trigger member having a surface positioned to be contacted by the hammer during rearward pivoting of the hammer to cause the trigger member to be forced to the set position, wherein the sear and sear catch are in engagement in the set positions of the hammer and trigger member and are out of engagement in the released positions of the hammer and trigger member, a disconnector having a hook for engaging the hammer and mounted in the fire control mechanism pocket to pivot on the transverse trigger member pivot axis, a locking member mounted in the fire control mechanism pocket to pivot on a transverse locking member pivot axis, the locking member being pivotable between a first position at which the locking member mechanically blocks the trigger member from moving to the released position and a second position at which the locking member does not mechanically block the trigger member allowing the trigger member to be moved to the released position, the locking member spring biased toward the first position and moved against the spring bias to the second position by contact from the bolt carrier during forward movement of the bolt carrier as the bolt carrier reaches a substantially in-battery position, and a safety selector adapted mounted in the fire control mechanism pocket to pivot between safe, standard semi-automatic, and forced reset semi-automatic positions. In the standard semi-automatic position, rearward movement of the bolt carrier causes rearward pivoting of the hammer such that the disconnector hook catches the hammer hook, at which time a user must manually release the trigger member to free the hammer from the disconnector to permit the hammer and trigger member to pivot to the set positions so that the user can pull the trigger member to fire the firearm. In the forced reset semi-automatic position, rearward movement of the bolt carrier causes rearward pivoting of the hammer causing the trigger member to be forced to the set position, the safety selector preventing the disconnector hook from catching the hammer hook, and thereafter when the bolt carrier reaches the substantially in-battery position the user can pull the trigger member to fire the firearm without manually releasing the trigger member.

The firearm can further comprise a housing having a first pair of transversely aligned openings with a hammer pin therethrough and a second pair of transversely aligned openings with a trigger member pin therethrough, the hammer mounted on the hammer pin, the trigger member and disconnector mounted on the trigger member pin. The firearm can further comprise the receiver having a first pair of transversely aligned assembly pin openings and a second pair of transversely aligned assembly pin openings, the housing first pair of openings coaxial with the receiver first pair of openings and the housing second pair of openings coaxial with the receiver second pair of openings, a first assembly pin passing through the receiver first pair of openings and through the housing first pair of openings, and a second assembly pin passing through the receiver second pair of openings and through the housing second pair of openings. The firearm can further include a spring which biases the trigger member towards the set position. The spring can be a compression spring positioned between a forward end of the trigger member and a floor of the housing.

In another aspect, a firearm trigger mechanism comprises a hammer having a sear catch and a hook for engaging a disconnector and adapted to be mounted in a fire control mechanism pocket of a receiver to pivot on a transverse hammer pivot axis between set and released positions, the hammer adapted to be pivoted rearward by rearward movement of a bolt carrier, a trigger member having a sear and adapted to be mounted in the fire control mechanism pocket to pivot on a transverse trigger member pivot axis between set and released positions, the trigger member having a surface positioned to be contacted by a surface of the hammer during rearward pivoting of the hammer to cause the trigger member to be forced to the set position, wherein the sear and sear catch are in engagement in the set positions of the hammer and trigger member and are out of engagement in the released positions of the hammer and trigger member, a disconnector having a hook for engaging the hammer and adapted to be mounted in the fire control mechanism pocket to pivot on the transverse trigger member pivot axis, a locking member adapted to be movably mounted in the fire control mechanism pocket, the locking member being movable between a first position at which the locking member mechanically blocks the trigger member from moving to the released position and a second position at which the locking member does not mechanically block the trigger member allowing the trigger member to be moved to the released position, the locking member spring biased toward the first position and adapted to be moved against the spring bias to the second position by contact from the bolt carrier during forward movement of the bolt carrier as the bolt carrier reaches a substantially in-battery position, and a safety selector adapted to be mounted in the fire control mechanism pocket to pivot between safe, standard semi-automatic, and forced reset semi-automatic positions. In the standard semi-automatic position, rearward movement of the bolt carrier causes rearward pivoting of the hammer such that the disconnector hook catches the hammer hook, at which time a user must manually release the trigger member to free the hammer from the disconnector to permit the hammer and trigger member to pivot to the set positions so that the user can pull the trigger member to fire the firearm. In the forced reset semi-automatic position, rearward movement of the bolt carrier causes rearward pivoting of the hammer causing the trigger member to be forced to the set position, the safety selector preventing the disconnector hook from catching the hammer hook, and thereafter when the bolt carrier reaches the substantially in-battery position the user can pull the trigger member to fire the firearm without manually releasing the trigger member.

Other aspects, features, benefits, and advantages of the present invention will become apparent to a person of skill in the art from the detailed description of various embodiments with reference to the accompanying drawing figures, all of which comprise part of the disclosure.

BRIEF DESCRIPTION OF THE DRAWINGS

Like reference numerals are used to indicate like parts throughout the various drawing figures, wherein.

DETAILED DESCRIPTION

Figure 1:
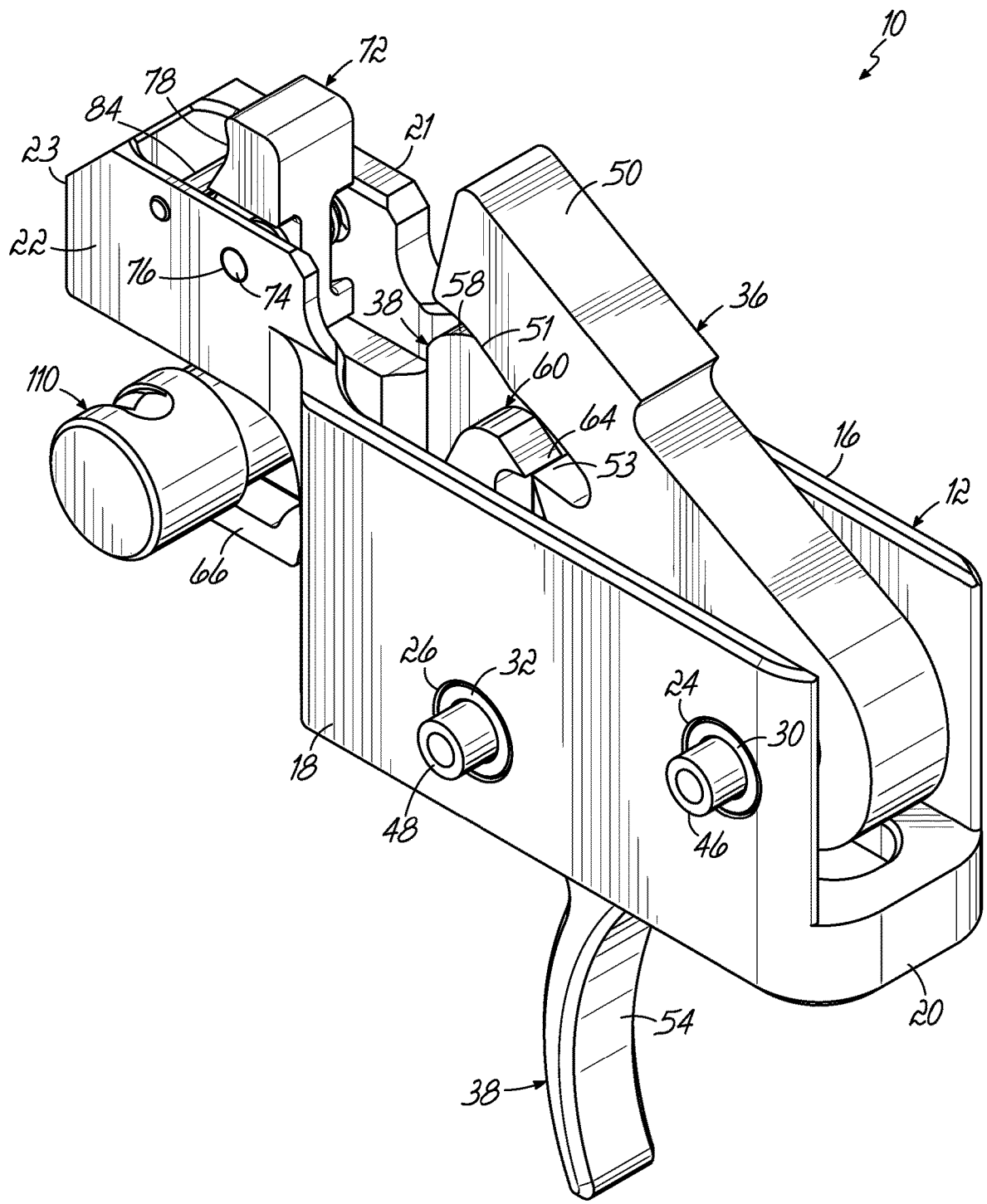
FIG. 1 is a top front right perspective view of a drop-in trigger module for an AR-pattern firearm according to one embodiment of the invention.
Figure 2:
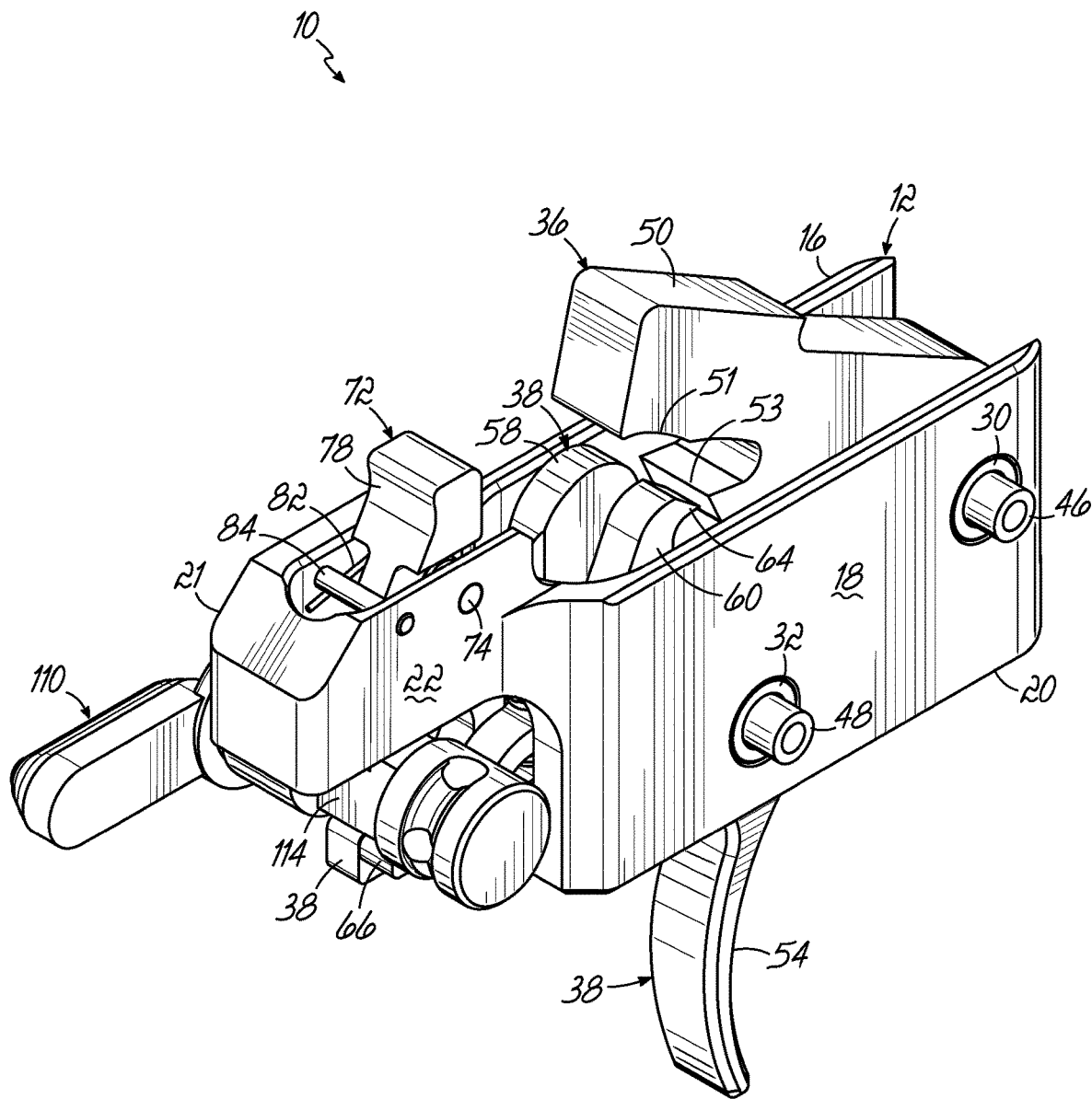
FIG. 2 is a top rear right perspective view thereof.
Figure 3:
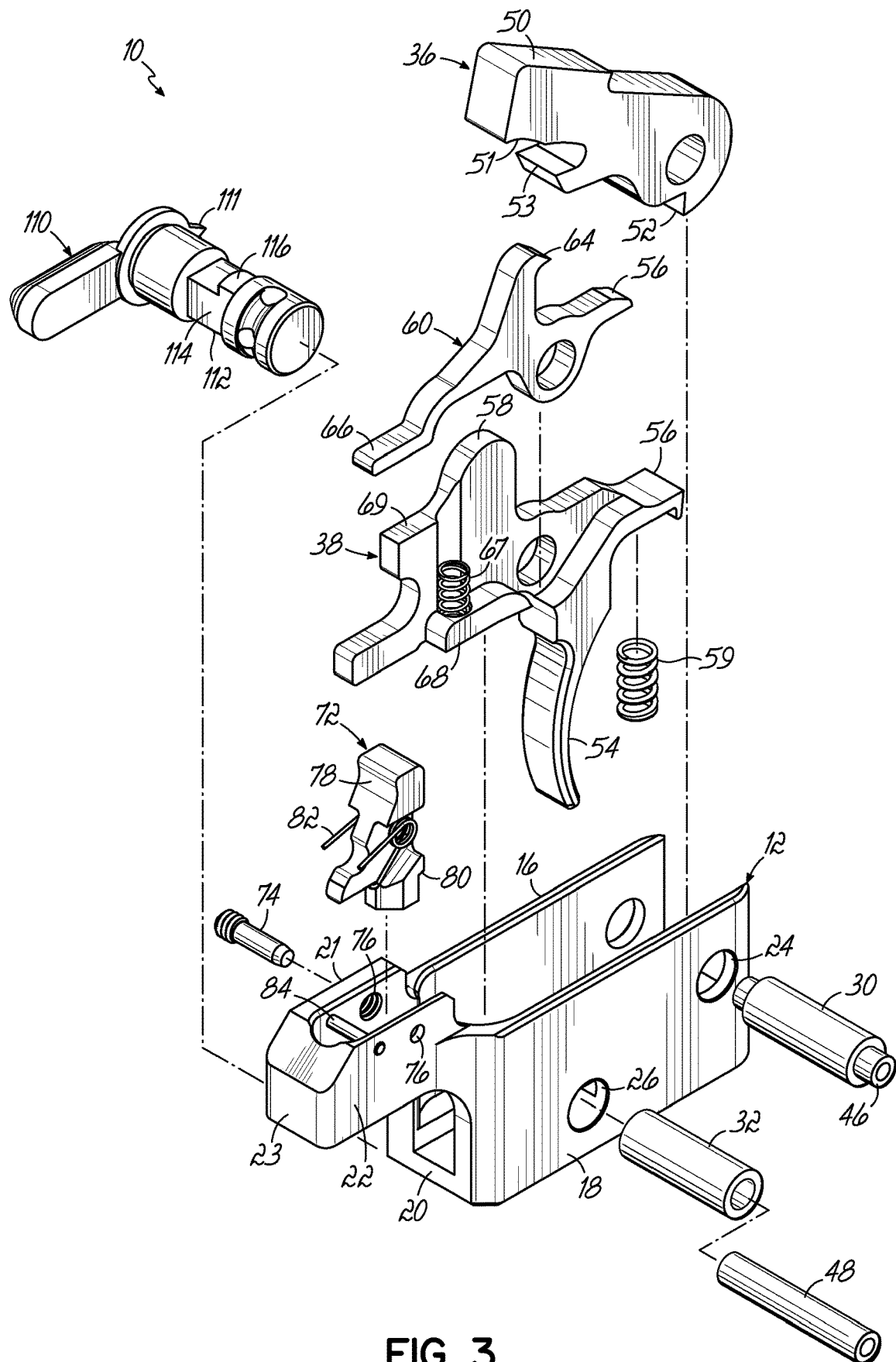
FIG. 3 is a top rear right exploded perspective view thereof.

With reference to the drawing figures, this section describes particular embodiments and their detailed construction and operation. Throughout the specification, reference to "one embodiment," "an embodiment," or "some embodiments" means that a particular described feature, structure, or characteristic may be included in at least one embodiment. Thus, appearances of the phrases "in one embodiment," "in an embodiment," or "in some embodiments" in various places throughout this specification are not necessarily all referring to the same embodiment. Furthermore, the described features, structures, and characteristics may be combined in any suitable manner in one or more embodiments. In view of the disclosure herein, those skilled in the art will recognize that the various embodiments can be practiced without one or more of the specific details or with other methods, components, materials, or the like. In some instances, well-known structures, materials, or operations are not shown or not described in detail to avoid obscuring aspects of the embodiments. "Forward" will indicate the direction of the muzzle and the direction in which projectiles are fired, while "rearward" will indicate the opposite direction. "Lateral" or "transverse" indicates a side-to-side direction generally perpendicular to the axis of the barrel. Although firearms may be used in any orientation, "left" and "right" will generally indicate the sides according to the user's orientation, "top" or "up" will be the upward direction when the firearm is gripped in the ordinary manner.

Referring first to FIGS. 1-6B, there is illustrated a "drop-in" trigger module 10 adapted for use in an AR-pattern firearm according to a first embodiment of the present invention. As used herein, "AR-pattern" firearm includes the semiautomatic versions of the AR10 and AR15 firearms and variants thereof of any caliber, including pistol caliber carbines or pistols using a blow-back bolt. While select fire (fully automatic capable) versions of this platform, such as the M16 and M4, are also AR-pattern firearms, this invention only relates to semiautomatic firearm actions. The concepts of this invention may be adaptable to other popular semiautomatic firearm platforms, such as the Ruger 10/22™, AK-pattern firearms, and HK-pattern firearms.

The module 10 includes a frame or housing 12 sized and shaped to fit within the internal fire control pocket of an AR-pattern lower receiver 14. Lower receiver parts not important to the present invention are well-known in the art and are omitted from the figures for clarity. The housing 12 includes forward left and right sidewalls 16, 18 which extend substantially vertically and parallel to one another in a laterally spaced-apart relationship. The sidewalls 16, 18 may be interconnected by a floor 20. Shorter, more narrowly spaced apart and substantially vertical and parallel rear sidewalls 21, 22 extend rearward from forward sidewalls 16, 18 and are interconnected by a rear end wall 23. The sidewalls 16, 18 include first and second pairs of aligned openings 24, 26 for receiving hollow transverse pins 30, 32 upon which a hammer 36 and trigger member 38 pivot. The openings 24, 26 are located coaxially with openings 42, 44 in the lower receiver 14. Standard AR-pattern hammer and trigger pins 46, 48 pass through the openings 42, 44 in the lower receiver 14 and through the hollow transverse pins 30, 32 to assemble the housing 12 into the lower receiver 14. Thus, the pins 30, 32 retain the hammer 36 and trigger member 38 in the housing 12 in modular fashion, whereas the pins 46, 48 retain the trigger module 10 in the lower receiver 14.

The hammer 36 has a hammer head 50, a sear catch 52, a hammer hook 53, and a concave contact surface 51. The hammer 36 is spring biased towards a forward position by a standard AR-pattern hammer torsion spring (not shown).

The trigger member 38 has a trigger blade 54 that extends downwardly. The trigger blade 54 is the part of the trigger member 38 contacted by a user's finger to actuate the trigger mechanism. The trigger blade 54 may be curved (as shown) or straight, as desired. The trigger member 38 has a sear 56. When the sear 56 and the sear catch 52 are engaged, the hammer 36 and trigger member 38 are in their set positions. When the sear 56 and sear catch 52 are not engaged, the hammer 36 and trigger member 38 are in their released positions. The trigger member 38 has a convex contact surface 58 that interacts with concave surface 51 on hammer 36 in a manner described below. The trigger member 38 also has a contact surface 69. The trigger member 38 is spring biased by a compression spring 59 positioned between a forward end of the trigger member 38 and the floor 20 of the housing 12 so that the trigger blade 54 is spring biased towards a forward position.

A disconnector 60 is pivoted on the hollow transverse pin 32 upon which the trigger member 38 pivots. The disconnector 60 has a disconnector hook 64 and a tail 66. The tail 66 of the disconnector 60 is spring biased upwardly away from a tail 68 of the trigger member 38 by a compression spring 67.

A locking or blocking member 72 is movably mounted to the housing 12. For example, the locking/blocking member 72 can be pivoted on a locking/blocking member pin or screw 74 that is installed in aligned openings 76 in the sidewalls 21, 22 of the housing 12. The locking member 72 has a first contact surface 78 that interacts with an engagement surface 94 in a rear portion 96 of a bolt carrier body 98 of a bolt carrier assembly 92, in a manner to be described below. The locking member 72 has a second contact surface 80 that interacts with surface 69 of trigger member 38 in a manner to be described below. The locking member 72 is spring biased by a torsion spring 82 acting between a pin 84 in the sidewalls 21, 22 and a lower portion of the locking member 72 such that surface 78 is biased rearward and surface 80 is biased forward. Alternatively, the locking/blocking member 72 can be slidably mounted to the housing 12 and spring biased forward by a compression spring.

An upper receiver 90 houses a bolt carrier assembly 92. As is well-known in the art, the bolt carrier assembly 92 (or blow-back bolt) slidably reciprocates in the upper receiver 90 and engages the breach of a barrel or barrel extension. As used herein, "bolt carrier" and "bolt carrier assembly" may be used interchangeably and include a blow-back type bolt used in pistol caliber carbine configurations of the AR-platform. The bolt carrier assembly 92 used with the embodiments of this invention can have either a standard mil-spec M16-pattern bolt carrier, a standard AR15-pattern bolt carrier, or some variation of the two, depending on the design of the locking member 72, and whether operated by a gas direct impingement system or a gas piston system. The bolt carrier assembly 92 has an engagement surface 94 in a rear portion 96 of the bolt carrier body 98. As in an ordinary AR15-pattern configuration, during rearward travel of the bolt carrier assembly 92 a lower surface 102 in a forward portion 104 of the bolt carrier body 98 contacts the face of the hammer head 50 causing the hammer 36 to pivot rearward. Rearward travel of bolt carrier assembly 92 also moves engagement surface 94 rearward and away from surface 78 of locking member 72. The action of spring 82 causes locking member 72 to pivot in a first direction from a first position wherein surface 80 of locking member 72 does not impede upward movement of surface 69 of trigger member 38 to a second position wherein surface 80 of locking member 72 does impede upward movement of surface 69 of trigger member 38 thus preventing the trigger blade 54 from being pulled by the user. During forward travel of the bolt carrier assembly 92 the engagement surface 94 of the bolt carrier body 98 contacts the surface 78 of the locking member 72 to pivot the locking member 72 in a second opposite direction from the second position to the first position.

Figure 4A:
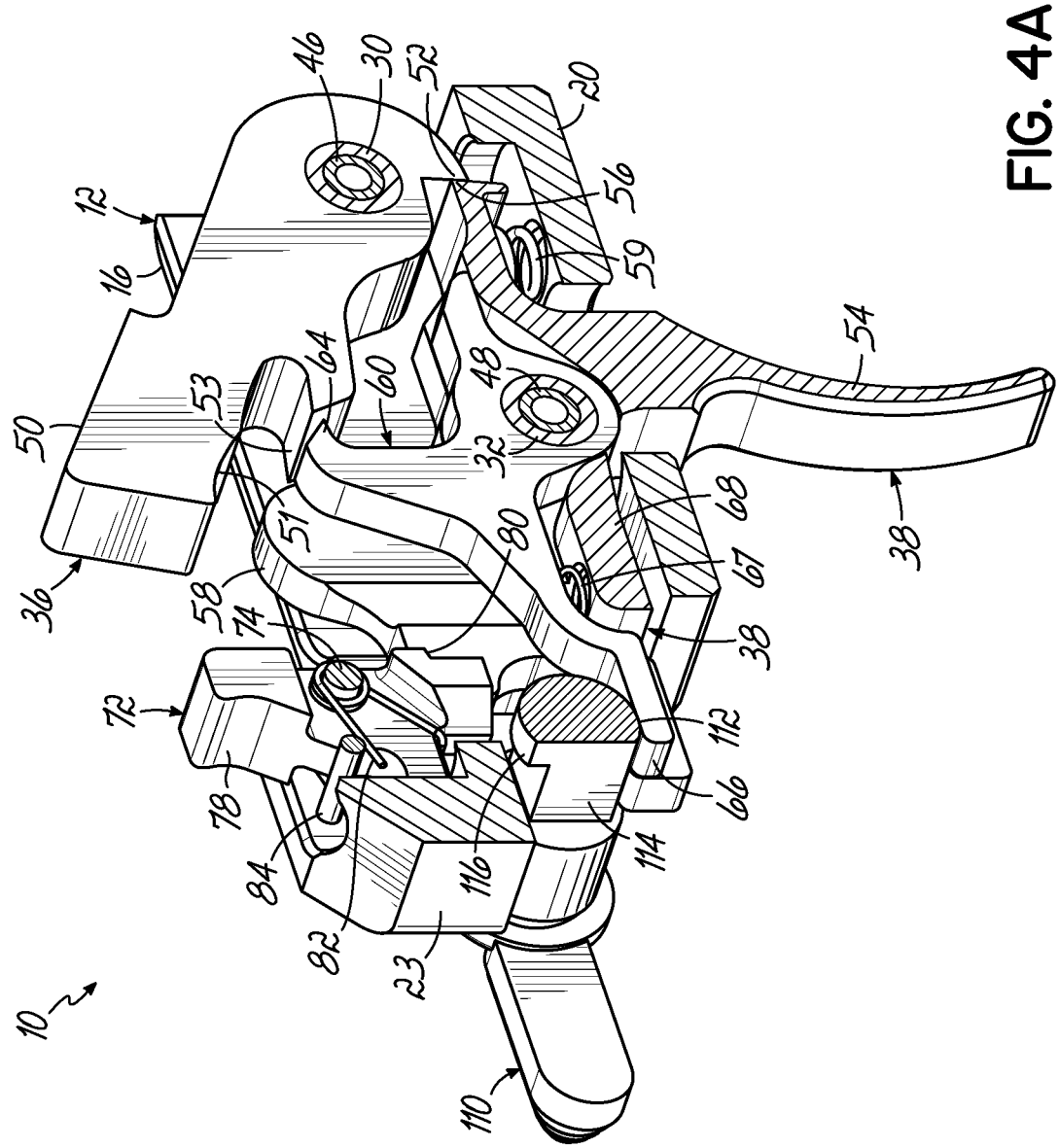
FIG. 4A is a top rear right cross-sectional view thereof with the safety selector in the safe position and with the hammer and trigger member in their set positions.
Figure 4B:
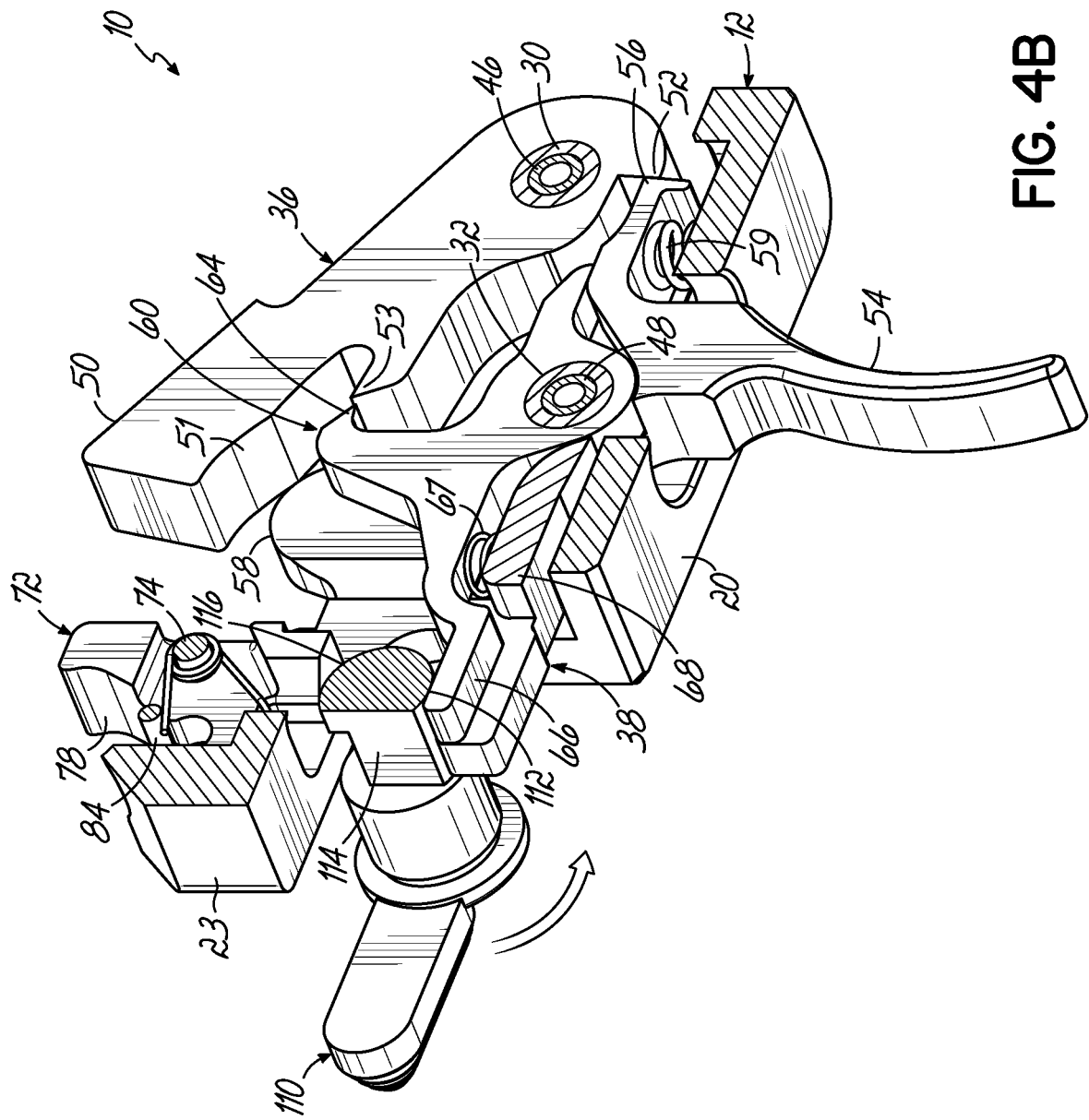
FIG. 4B is a bottom rear right cross-sectional view thereof with the safety selector in the safe position and with the hammer and trigger member in their set positions.
Figure 5A:
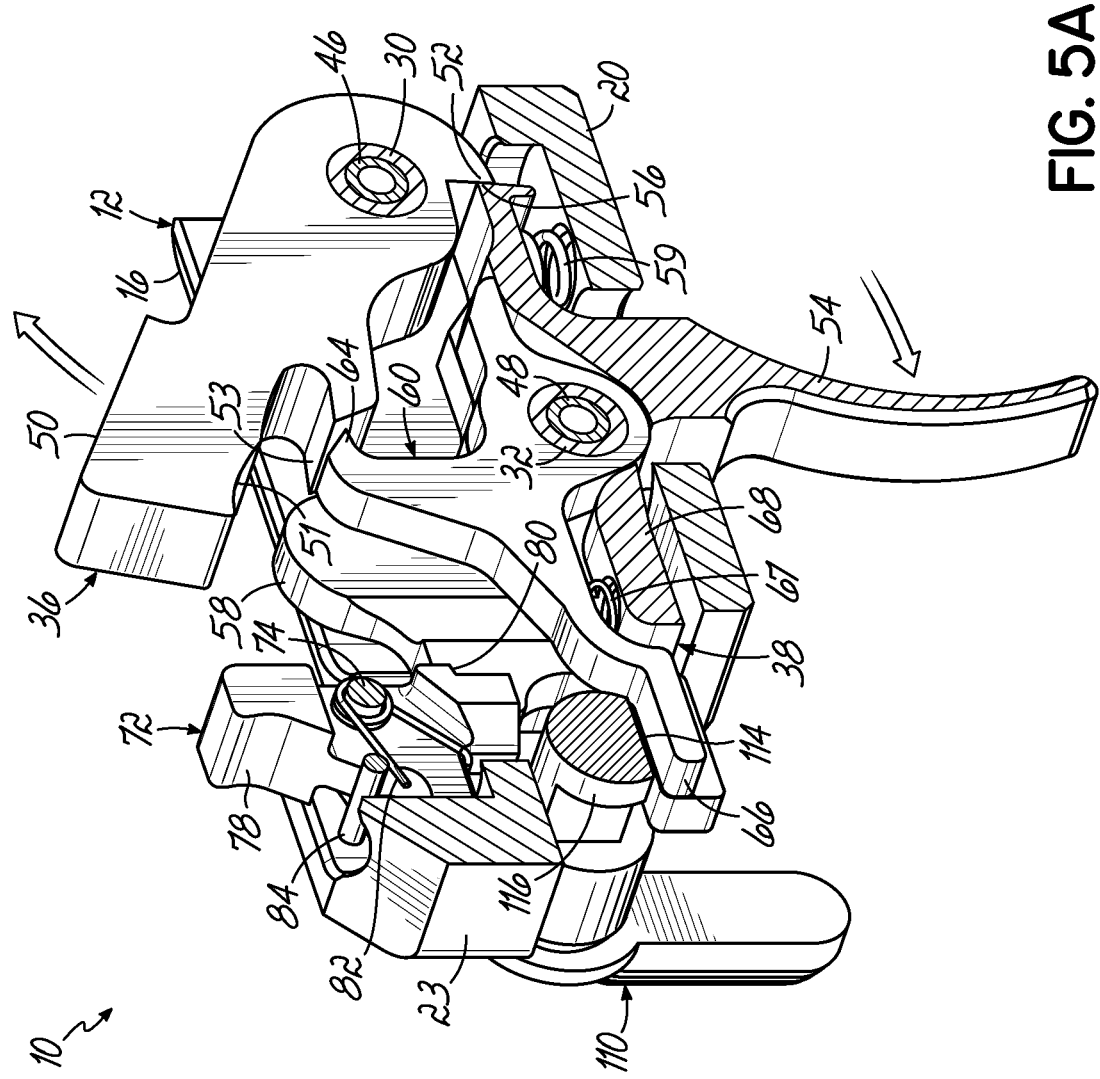
FIG. 5A is a top rear right cross-sectional view thereof with the safety selector in the standard semi-automatic position and with the hammer and trigger member in their set positions.
Figure 5B:
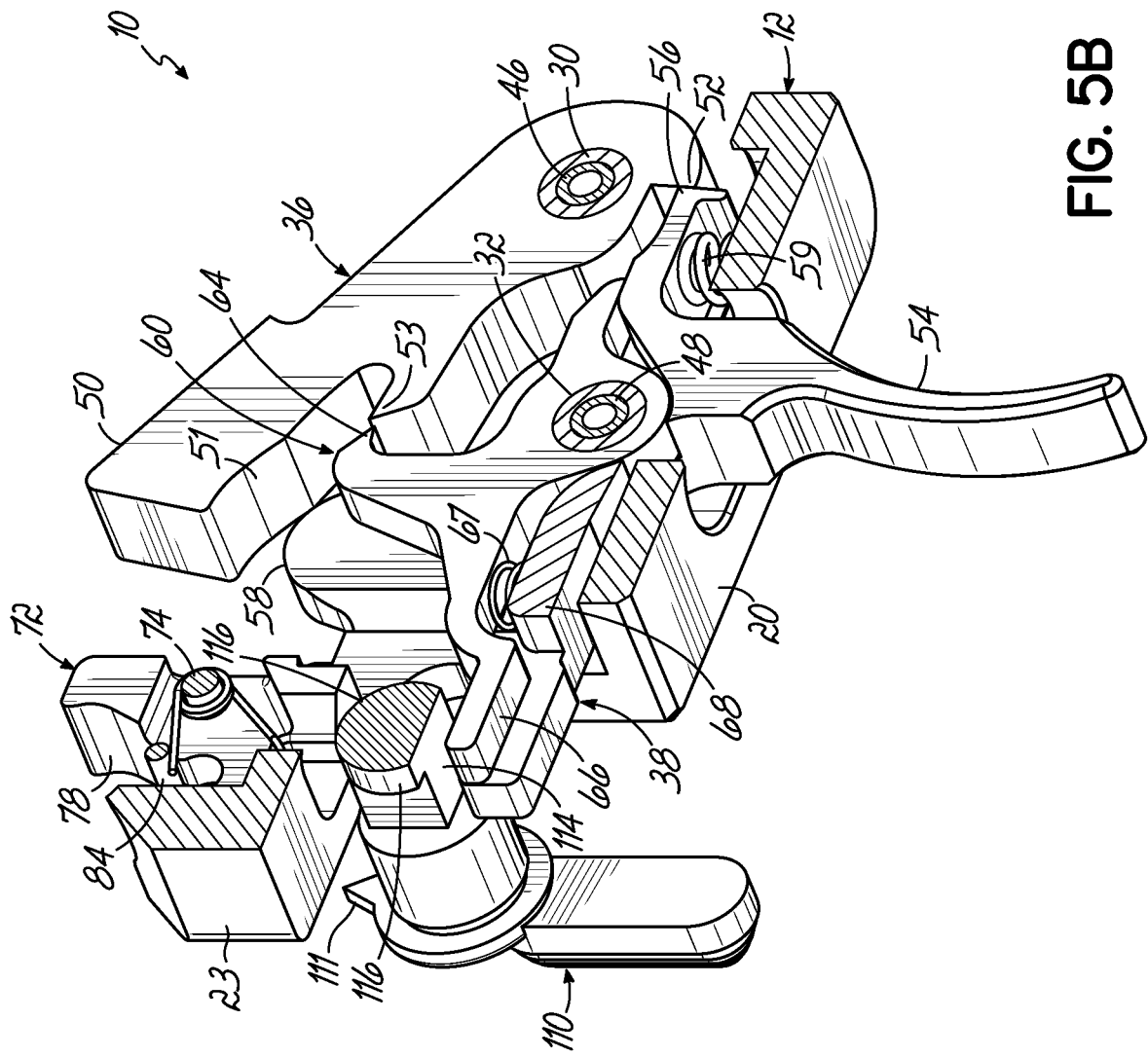
FIG. 5B is a bottom rear right cross-sectional view thereof with the safety selector in the standard semi-automatic position and with the hammer and trigger member in their set positions.
Figure 6A:
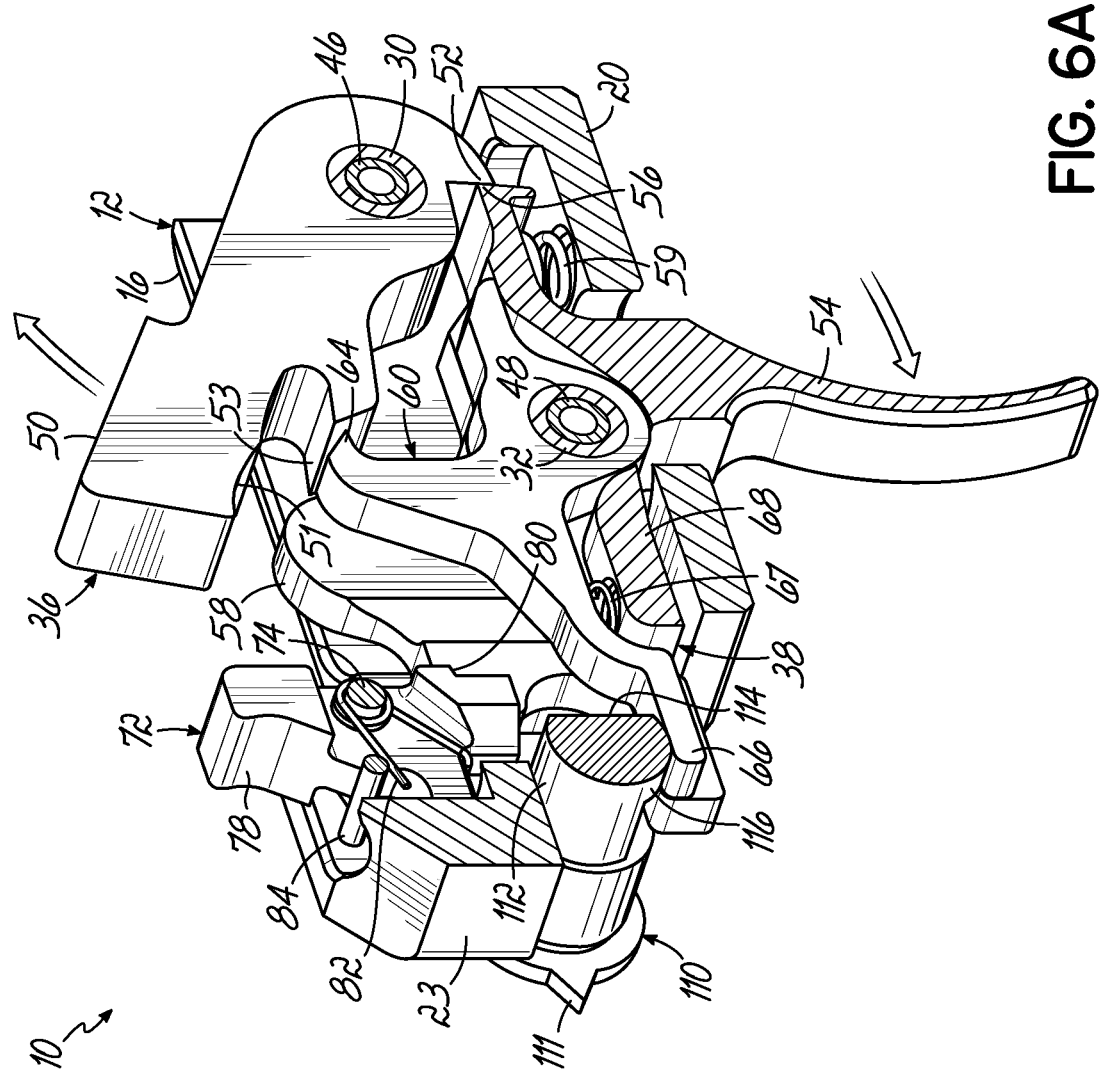
FIG. 6A is a top rear right cross-sectional view thereof with the safety selector in the forced reset semi-automatic position and with the hammer and trigger member in their set positions.
Figure 6B:
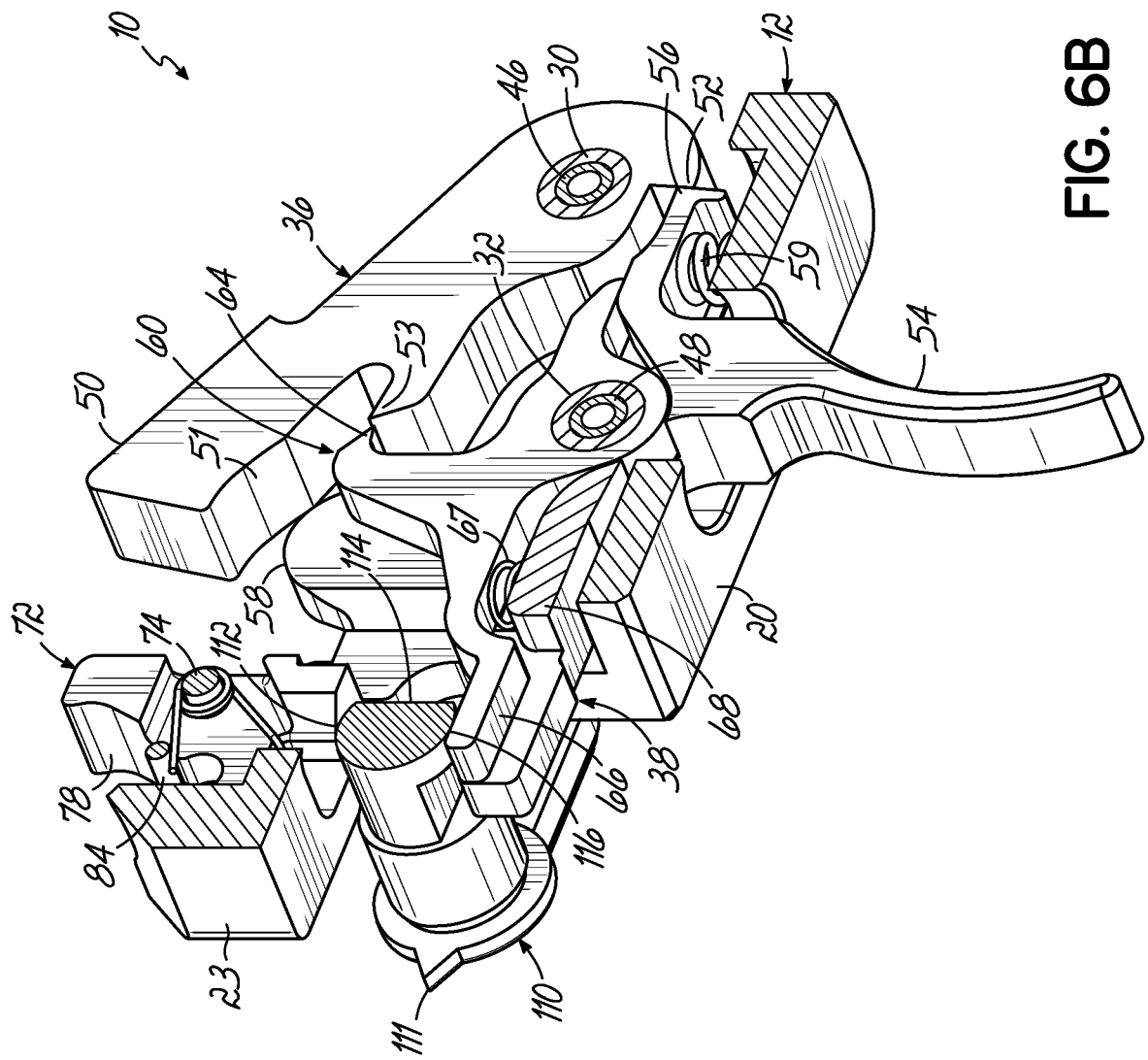
FIG. 6B is a bottom rear right cross-sectional view thereof with the safety selector in the forced reset semi-automatic position and with the hammer and trigger member in their set positions.
Figure 7:
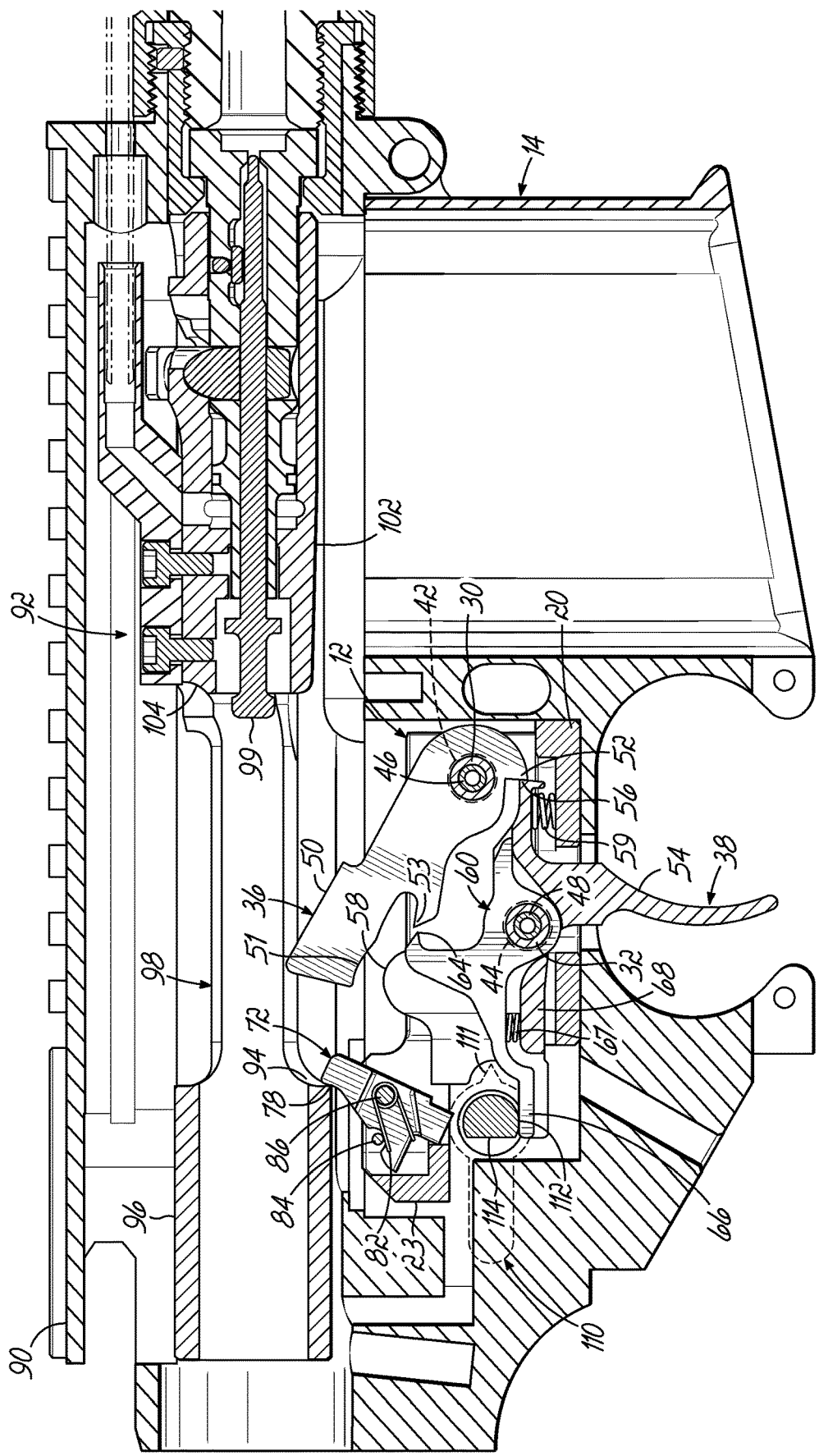
FIG. 7 is a cross-sectional view showing the trigger module installed in a typical AR15-pattern lower receiver, with the hammer and trigger member in their set positions and with the bolt carrier in an in-battery position, and with the safety selector in the safe position.
Figure 8A:
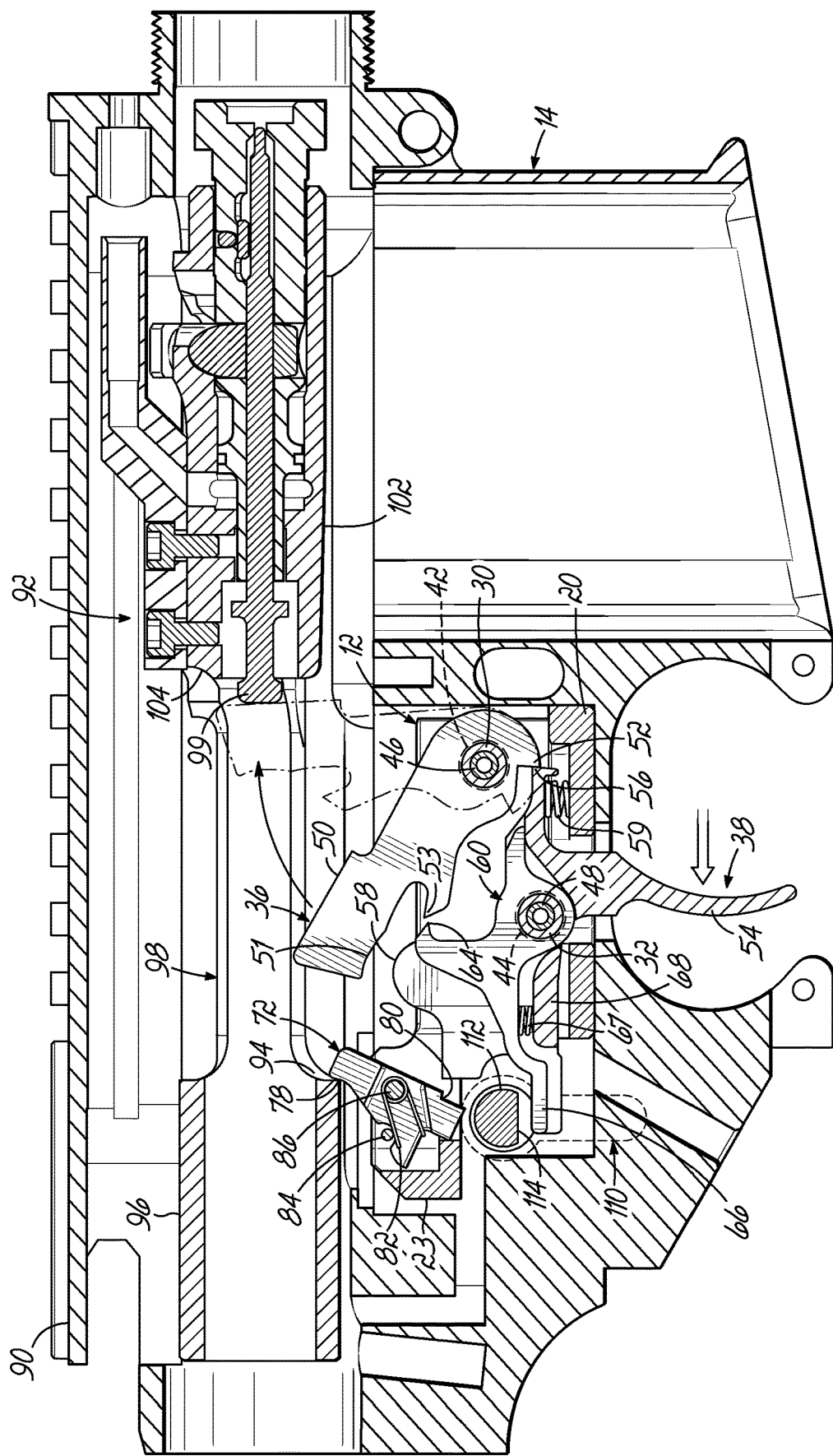
FIG. 8A is a view similar to FIG. 7 but with the safety selector in the standard semi-automatic position.
Figure 8B:
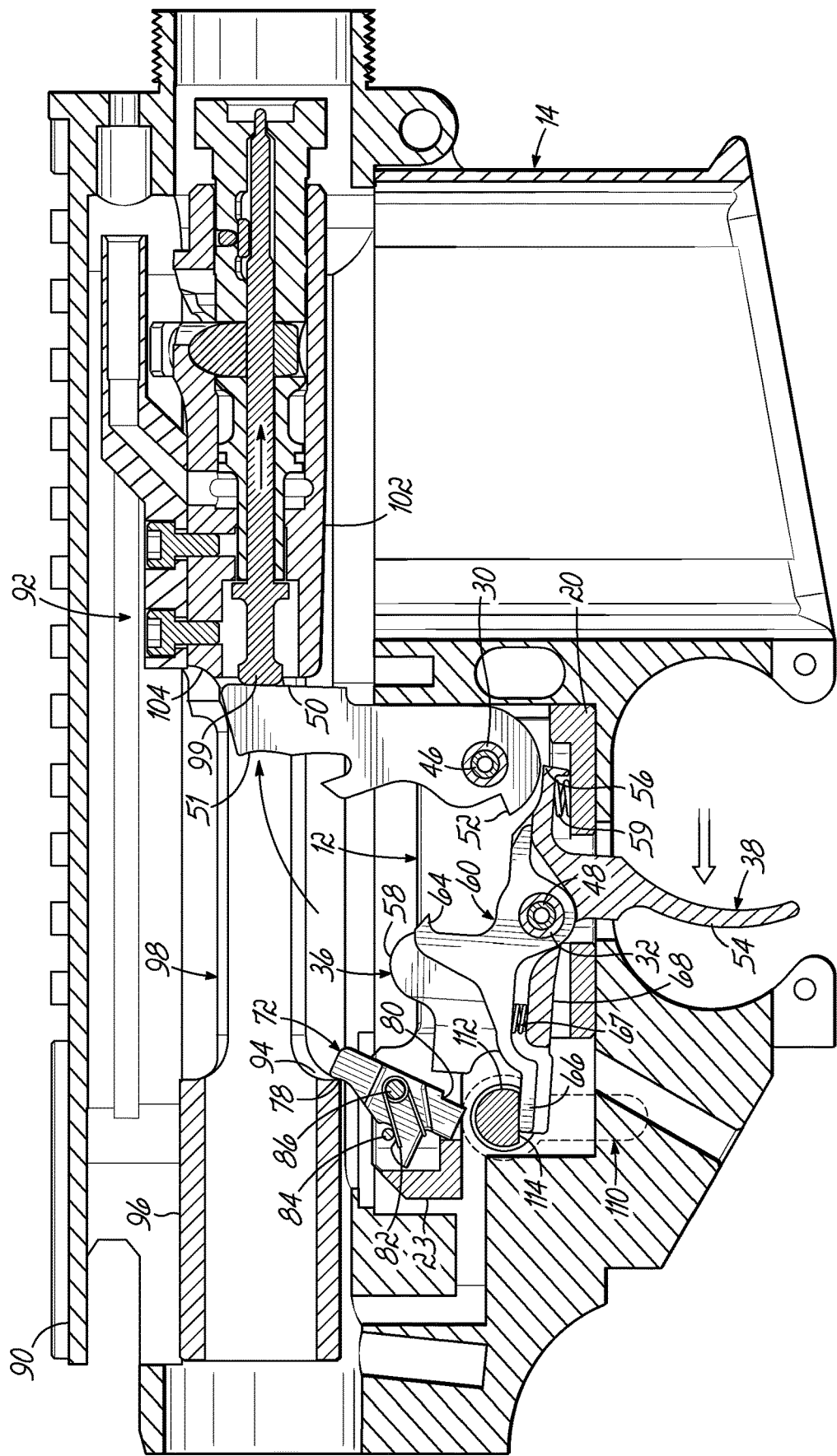
FIG. 8B is a view similar to FIG. 8A but after the trigger has been pulled to drop the hammer.
Figure 8C:
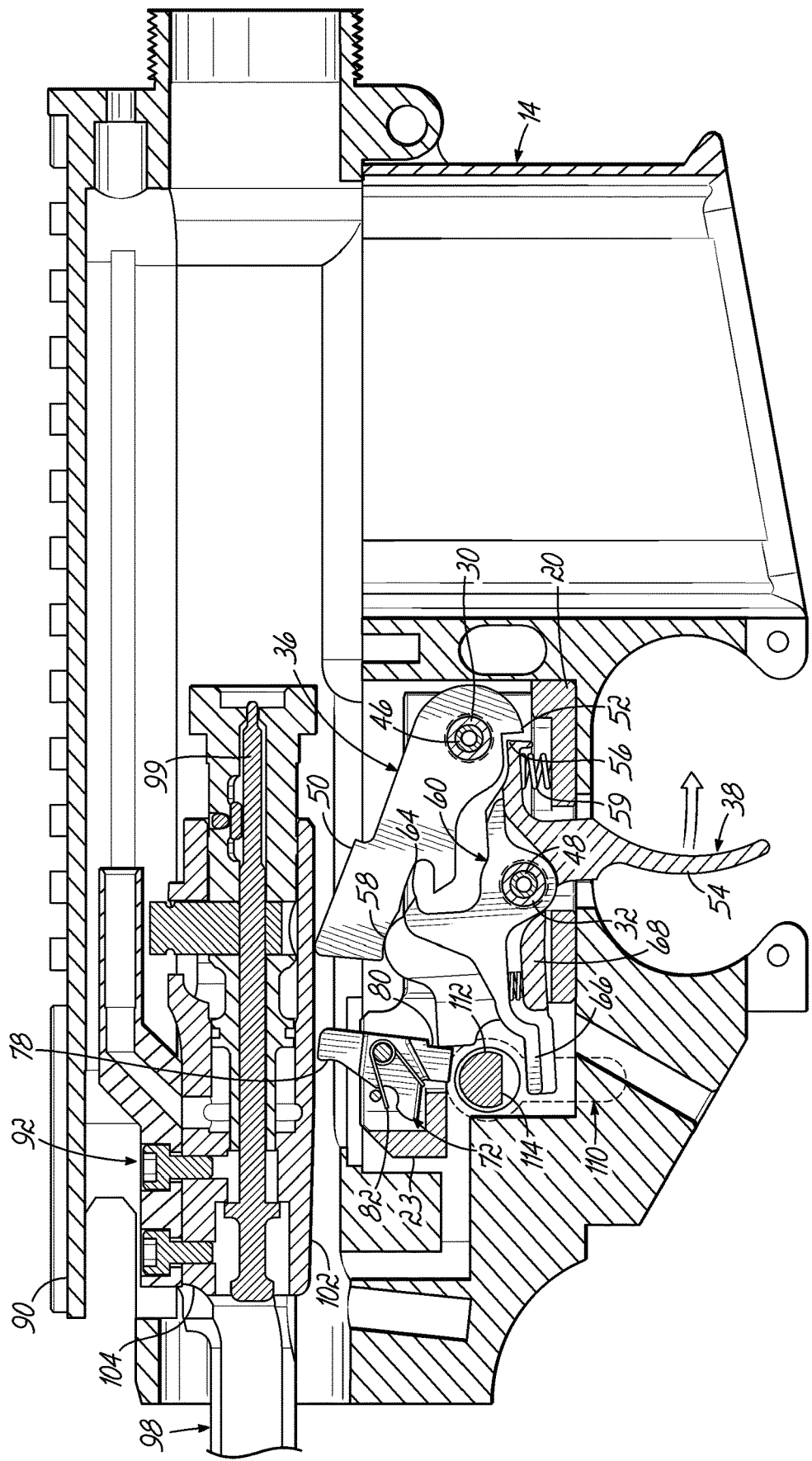
FIG. 8C is a view similar to FIG. 8B but with the bolt carrier cycling to the rear to pivot the hammer.
Figure 8D:
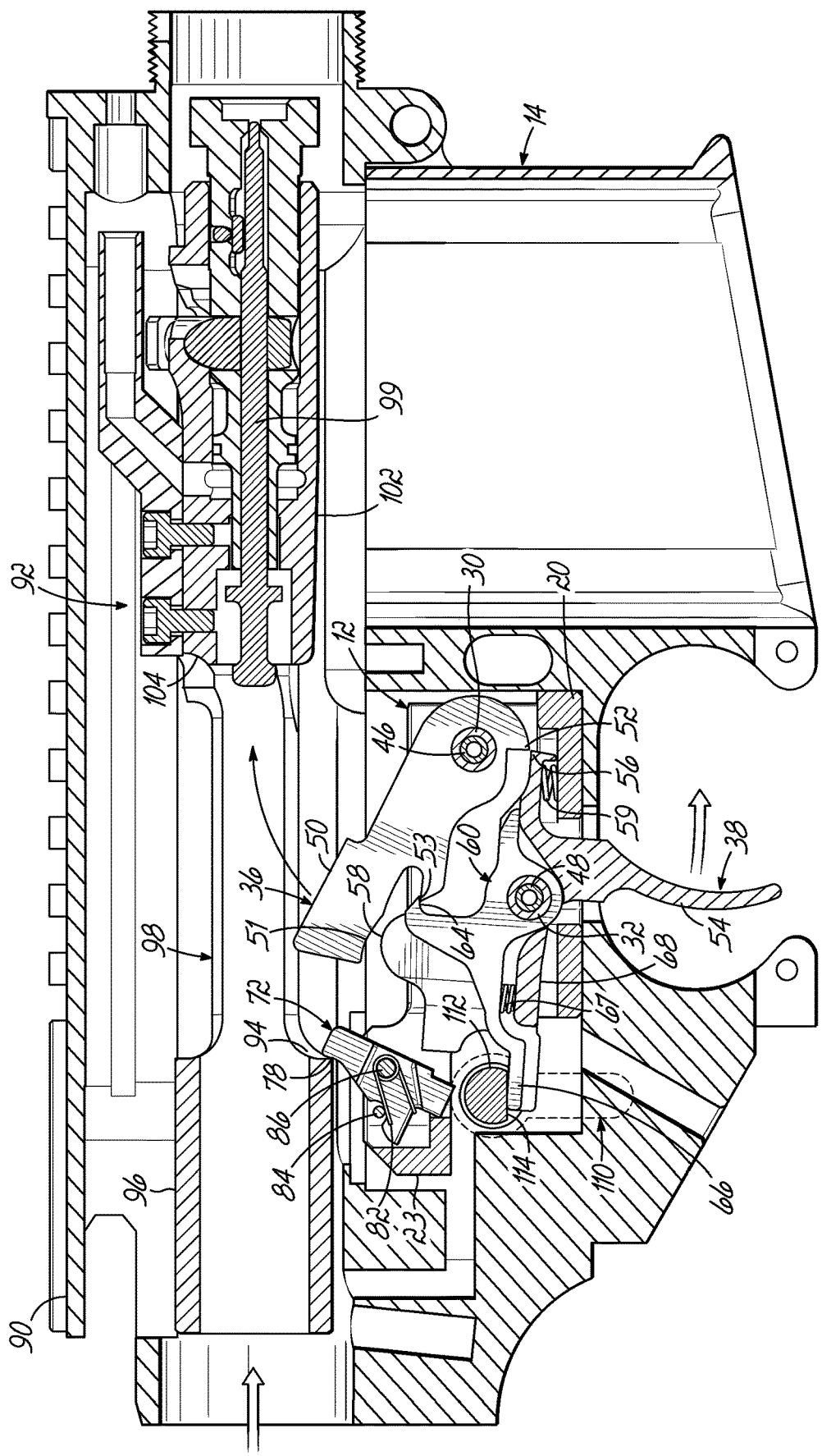
FIG. 8D is a view similar to FIG. 8C but with the bolt carrier having returned to battery and the disconnector having caught the hammer.
Figure 9A:
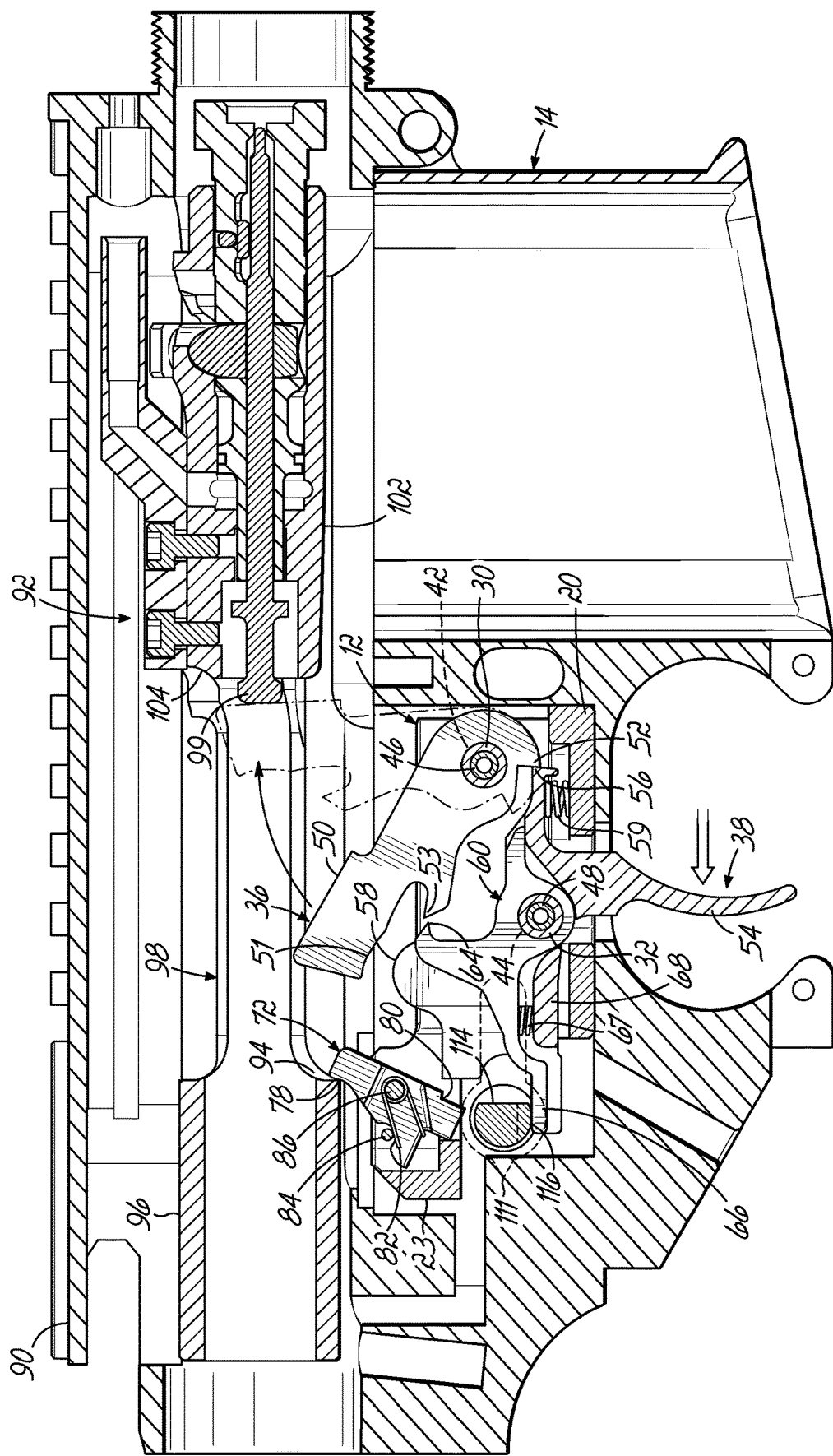
FIG. 9A is a view similar to FIG. 7 but with the safety selector in the forced reset semi-automatic position.
Figure 9B:
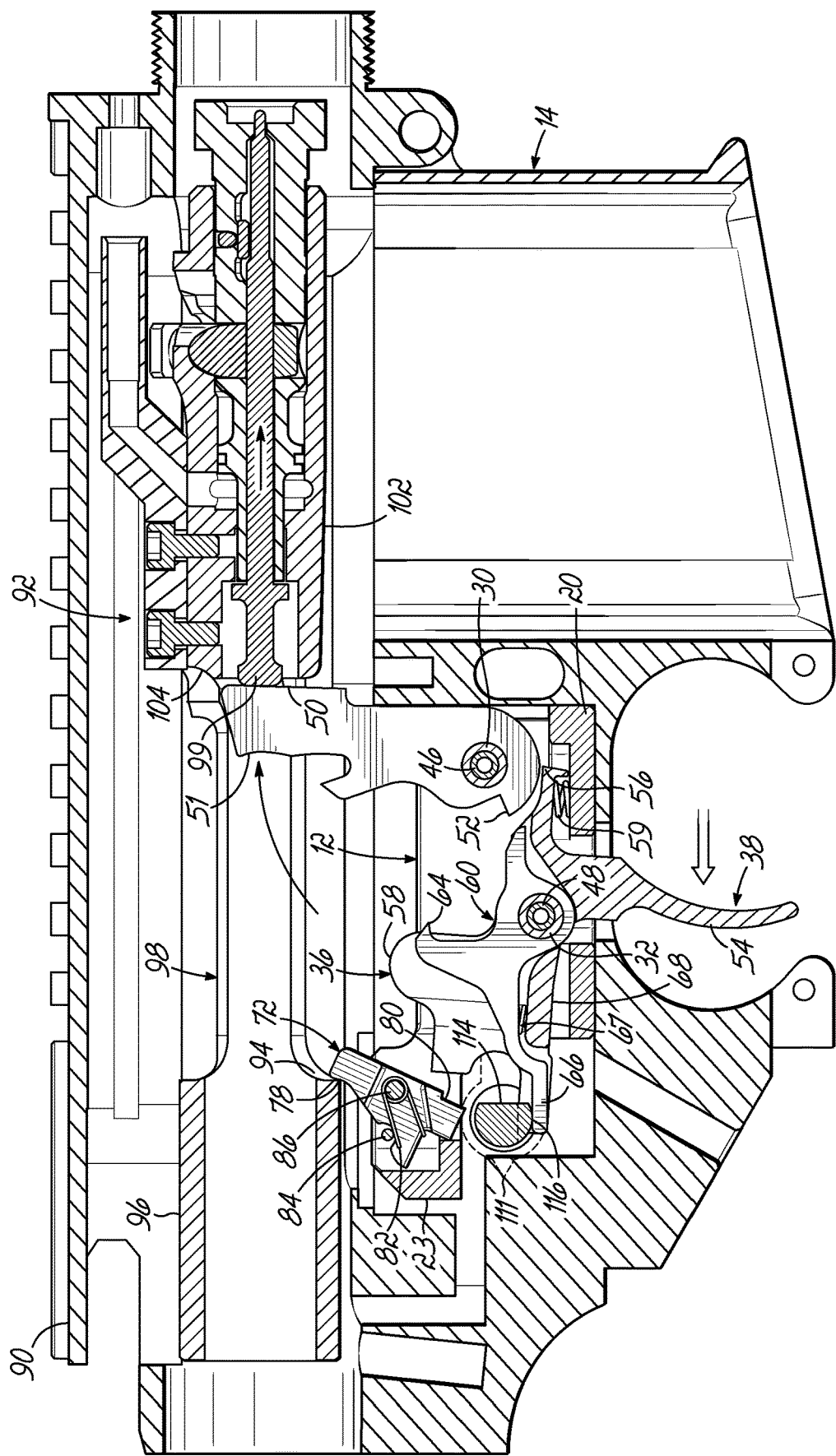
FIG. 9B is a view similar to FIG. 9A but after the trigger has been pulled to drop the hammer.
Figure 9C:
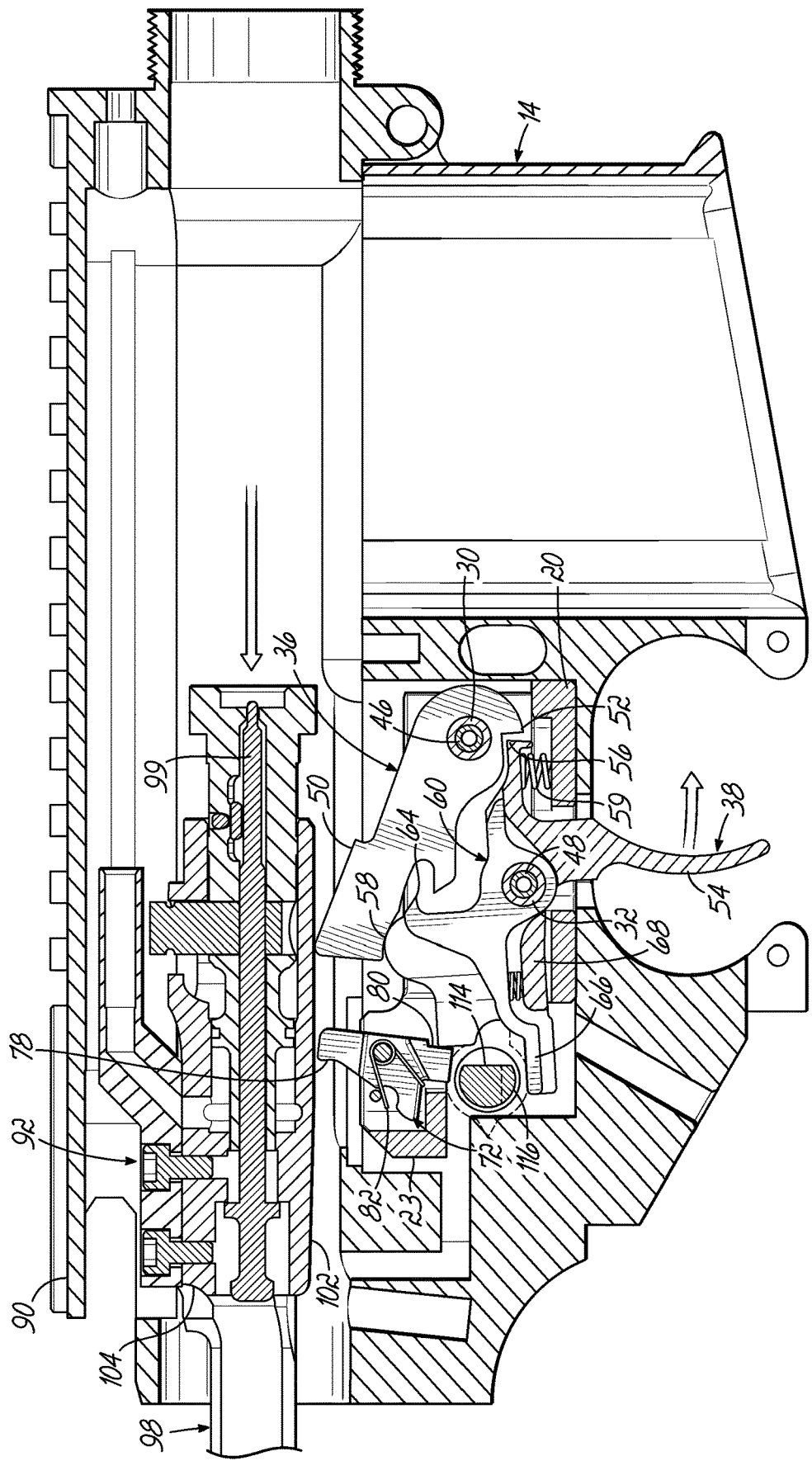
FIG. 9C is a view similar to FIG. 9B but with the bolt carrier cycling to the rear to pivot the hammer.
Figure 9D:
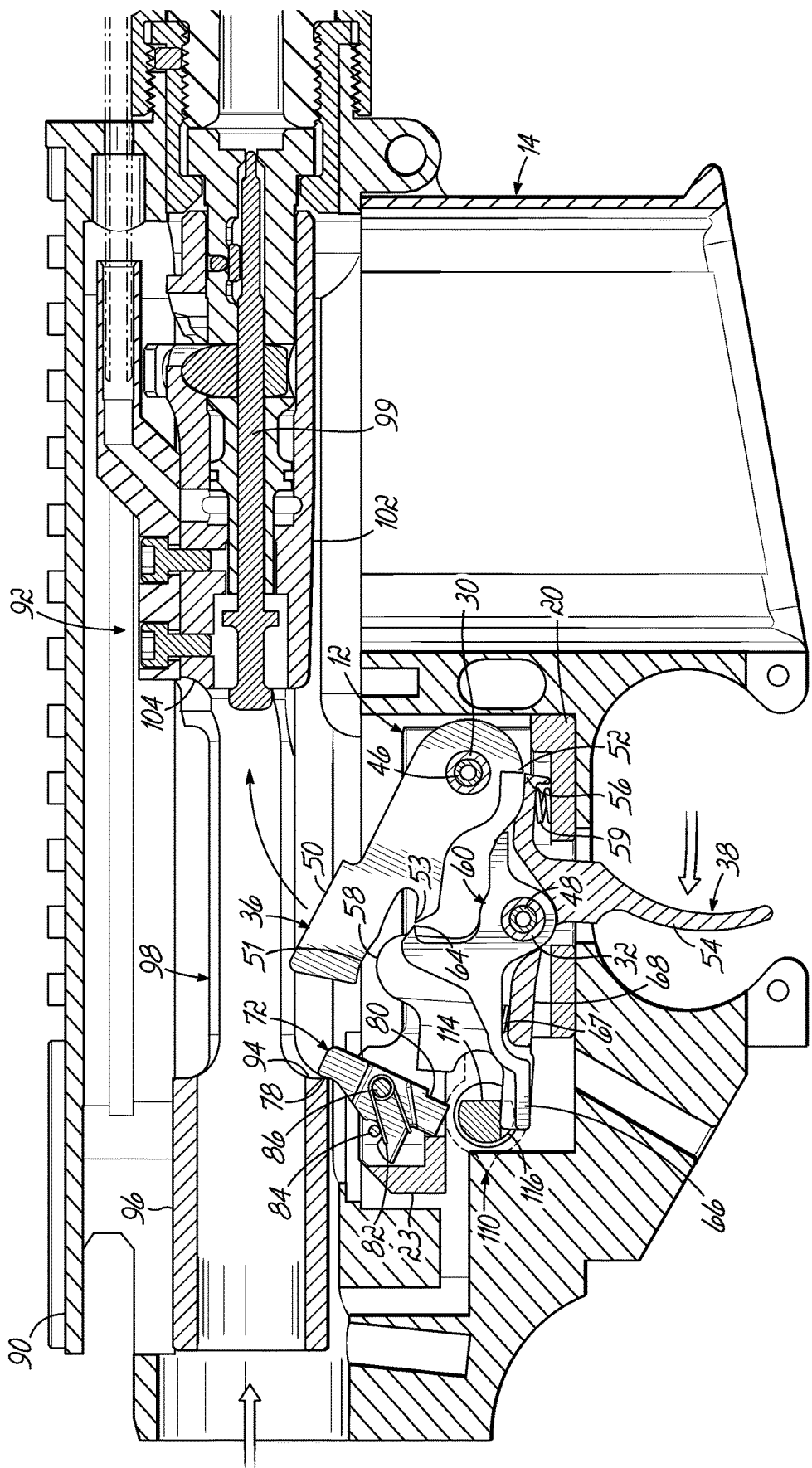
FIG. 9D is a view similar to FIG. 9C but with the bolt carrier having returned to battery and the hammer and trigger having returned to their set positions.

A three position safety selector 110 has safe, standard semi-automatic, and forced reset semi-automatic positions. When in the safe position (safety selector indicator 111 pointing forward), a wide semi-circular portion 112 of the safety selector 110 prevents the trigger blade 54 from being pulled (FIGS. 4A, 4B, and 7). When in the standard semi-automatic position (safety selector indicator 111 pointing upward), a flat portion 114 of the safety selector 110 permits the trigger blade 54 to be pulled. The disconnector 60 can pivot with the trigger member 38 and the disconnector hook 64 can catch the hammer hook 53 during rearward pivoting travel of the hammer head 50. (FIGS. 5A and 5B). When in the forced reset semi-automatic position (safety selector indicator 111 pointing rearward), a narrow semi-circular portion 116 permits the trigger blade 54 to be pulled but prevents the disconnector 60 from pivoting with the trigger member 38 thus preventing the disconnector hook 64 from catching the hammer hook 53 during rearward pivoting travel of the hammer head 50. (FIGS. 6A and 6B). In other words, in the forced reset semi-automatic position, the disconnector 60 is "disabled" in that the disconnector hook 64 is unable to catch the hammer hook 53 during cycling of the bolt carrier assembly 92.

Referring now to FIGS. 8A-8D, with the safety selector 110 set in the standard semi-automatic position, rearward finger pressure on the trigger blade 54 causes the trigger member 38 to rotate clockwise. Rotation of the trigger member 38 causes the sear 56 to disengage from the sear catch 52 of the hammer 36. This allows the hammer 36 to drop by spring force onto the firing pin 99 of the bolt carrier assembly 92, discharging an ammunition cartridge (not shown), and causing the action to cycle by moving the bolt carrier assembly 92 rearward. Rearward travel of the bolt carrier assembly 92 frees the locking member 72 to pivot such that surface 80 is moved into a blocking position. Rearward travel of the bolt carrier assembly 92 also causes the lower surface 102 to contact the face of the hammer head 50 and pivot the hammer 36 counter-clockwise. During pivoting travel of the hammer 36 surface 51 contacts surface 58 of trigger member 38 forcing trigger member 38 to pivot counter-clockwise. Also during pivoting travel of the hammer 36 the disconnector hook 64 catches the hammer hook 53. Forward travel of the bolt carrier assembly 92 returning to battery causes the surface 94 to contact the surface 78 of the locking member 72 to pivot the locking member 72 clockwise moving surface 80 out of the blocking position. At this point rearward finger pressure on the trigger blade 54 must be released to allow the sear 56 to engage the sear catch 52, returning the hammer 36 and trigger member 38 to their set positions. Thereafter the user can reapply rearward finger pressure on the trigger blade 54 to fire another round.

Referring now to FIGS. 9A-9D, with the safety selector 110 set in the forced reset semi-automatic position, rearward finger pressure on the trigger blade 54 causes the trigger member 38 to rotate clockwise. The narrow semi-circular portion 116 of the safety selector 110 prevents the disconnector 60 from rotating with the trigger member 38, thus "disabling" the disconnector 60, preventing the disconnector hook 64 from catching the hammer hook 53. Rotation of the trigger member 38 causes the sear 56 to disengage from the sear catch 52 of the hammer 36. This allows the hammer 36 to drop by spring force onto the firing pin 99 of the bolt carrier assembly 92, discharging an ammunition cartridge, and causing the action to cycle by moving the bolt carrier assembly 92 rearward. Rearward travel of the bolt carrier assembly 92 frees the locking member 72 to pivot such that surface 80 is moved into a blocking position. Rearward travel of the bolt carrier assembly 92 also causes the lower surface 102 to contact the face of the hammer head 50 and pivot the hammer 36 counter-clockwise. During pivoting travel of the hammer 36 surface 51 contacts surface 58 of trigger member 38 forcing trigger member 38 to pivot counter-clockwise. The bolt carrier assembly 92 thereby forces the hammer 36 and trigger member 38 to their set positions wherein the sear 56 engages the sear catch 52. Forward travel of the bolt carrier assembly 92 returning to battery causes the surface 94 to contact the surface 78 of the locking member 72 to pivot the locking member 72 clockwise. At this point the user can reapply rearward finger pressure on the trigger blade 54 to fire another round, without first manually releasing rear finger pressure on the trigger blade 54.

Thus, as the bolt carrier assembly 92 returns forward, the trigger member 38 is held in its set position by the locking member 72. The trigger member 38 cannot be pulled to release the sear/sear catch engagement, thus precluding early hammer release or "hammer follow" against the bolt carrier assembly 92 and firing pin 99 as the bolt carrier assembly 92 is returning to battery. When the bolt carrier assembly 92 has reached (or nearly reached) its closed, in-battery position, the engagement surface 94 contacts and forwardly displaces the contact surface 78 of the locking member 72, disengaging the contact surface 80 of the locking member 72 from the contact surface 69 of the trigger member 38, allowing the trigger blade 54 to be pulled. Again, this prevents early hammer release and contact of the hammer against the firing pin before the bolt is completely locked and in-battery.

While various embodiments of the present invention have been described in detail, it should be apparent that modifications and variations thereto are possible, all of which fall within the true spirit and scope of the invention. Therefore, the foregoing is intended only to be illustrative of the principles of the invention. The invention resides in each individual feature described herein, alone, and in any and all combinations and subcombinations of any and all of those features. Further, since numerous modifications and changes will readily occur to those skilled in the art, it is not intended to limit the invention to the exact construction and operation shown and described. Accordingly, all suitable modifications and equivalents may be included and considered to fall within the scope of the invention, defined by the following claim or claims.

What is claimed is:

1. A firearm trigger mechanism comprising:
   a hammer having a sear catch and a hook for engaging a disconnector and adapted to be mounted in a fire control mechanism pocket of a receiver to pivot on a transverse hammer pivot axis between set and released positions, said hammer adapted to be pivoted rearward by rearward movement of a bolt carrier,
   a trigger member having a sear and adapted to be mounted in the fire control mechanism pocket to pivot on a transverse trigger member pivot axis between set and released positions, said trigger member having a surface positioned to be contacted by a surface of said hammer during rearward pivoting of said hammer to cause said trigger member to be forced to said set position, wherein said sear and sear catch are in engagement in said set positions of said hammer and trigger member and are out of engagement in said released positions of said hammer and trigger member, a disconnector having a hook for engaging said hammer and adapted to be mounted in the fire control mechanism pocket to pivot on said transverse trigger member pivot axis, a locking member adapted to be mounted in the fire control mechanism pocket to pivot on a transverse locking member pivot axis, said locking member being pivotable between a first position at which said locking member mechanically blocks said trigger member from moving to said released position and a second position at which said locking member does not mechanically block said trigger member allowing said trigger member to be moved to said released position, said locking member spring biased toward said first position and adapted to be moved against said spring bias to said second position by contact from the bolt carrier during forward movement of the bolt carrier as the bolt carrier reaches a substantially in-battery position, and a safety selector adapted to be mounted in the fire control mechanism pocket to pivot between safe, standard semi-automatic, and forced reset semi-automatic positions, whereupon in said standard semi-automatic position, rearward movement of the bolt carrier causes rearward pivoting of said hammer such that said disconnector hook catches said hammer hook, at which time a user must manually release said trigger member to free said hammer from said disconnector to permit said hammer and trigger member to pivot to said set positions so that the user can pull said trigger member to fire the firearm, and whereupon in said forced reset semi-automatic position, rearward movement of the bolt carrier causes rearward pivoting of said hammer causing said trigger member to be forced to said set position, said safety selector preventing said disconnector hook from catching said hammer hook, and thereafter when the bolt carrier reaches the substantially in-battery position the user can pull said trigger member to fire the firearm without manually releasing said trigger member.

2. The trigger mechanism of claim 1, wherein said safety selector has a protuberance thereon which, when said safety selector is in said forced reset semi-automatic position, contacts said disconnector preventing said disconnector hook from catching said hammer hook.

3. The trigger mechanism of claim 1 further including a spring which biases said trigger member towards said set position.

4. A firearm trigger mechanism comprising:
a housing having a first pair of transversely aligned openings for receiving a hammer pin and a second pair of transversely aligned openings for receiving a trigger member pin,
a hammer having a sear catch and a hook for engaging a disconnector and mounted in said housing to pivot on said hammer pin between set and released positions, said hammer adapted to be pivoted rearward by rearward movement of a bolt carrier, a trigger member having a sear and mounted in said housing to pivot on said trigger member pin between set and released positions, said trigger member having a surface positioned to be contacted by a surface of said hammer during rearward pivoting of said hammer to cause said trigger member to be forced to said set position, wherein said sear and sear catch are in engagement in said set positions of said hammer and trigger member and are out of engagement in said released positions of said hammer and trigger member, a disconnector having a hook for engaging said hammer and mounted in said housing to pivot on said trigger member pin, a locking member mounted in said housing to pivot on a transverse locking member pin, said locking member being pivotable between a first position at which said locking member mechanically blocks said trigger member from moving to said released position and a second position at which said locking member does not mechanically block said trigger member allowing said trigger member to be moved to said released position, said locking member spring biased toward said first position and adapted to be moved against said spring bias to said second position by contact from the bolt carrier during forward movement of the bolt carrier as the bolt carrier reaches a substantially in-battery position, and a safety selector adapted to be mounted in a fire control mechanism pocket of a receiver to pivot between safe, standard semi-automatic, and forced reset semi-automatic positions, whereupon in said standard semi-automatic position, rearward movement of the bolt carrier causes rearward pivoting of said hammer such that said disconnector hook catches said hammer hook, at which time a user must manually release said trigger member to free said hammer from said disconnector to permit said hammer and trigger member to pivot to said set positions so that the user can pull said trigger member to fire the firearm, and whereupon in said forced reset semi-automatic position, rearward movement of the bolt carrier causes rearward pivoting of said hammer causing said trigger member to be forced to said set position, said safety selector preventing said disconnector hook from catching said hammer hook, and thereafter when the bolt carrier reaches the substantially in-battery position the user can pull said trigger member to fire the firearm without manually releasing said trigger member.

5. The trigger mechanism of claim 4, wherein said safety selector has a protuberance thereon which, when said safety selector is in said forced reset semi-automatic position, contacts said disconnector preventing said disconnector hook from catching said hammer hook.

6. The trigger mechanism of claim 4, wherein said first and second pairs of openings in said housing are adapted to be aligned with first and second pairs of transversely aligned assembly pin openings in the fire control mechanism pocket.

7. The trigger mechanism of claim 4 further including a spring which biases said trigger member towards said set position.

8. The trigger mechanism of claim 7 wherein said spring is a compression spring positioned between a forward end of said trigger member and a floor of said housing.

9. A firearm comprising:
a receiver having a fire control mechanism pocket therein,
a reciprocating bolt carrier,
a hammer having a sear catch and a hook for engaging a disconnector and mounted in said fire control mechanism pocket to pivot on a transverse hammer pivot axis between set and released positions, said hammer pivoted rearward by rearward movement of said bolt carrier,
a trigger member having a sear and mounted in said fire control mechanism pocket to pivot on a transverse trigger member pivot axis between set and released positions, said trigger member having a surface positioned to be contacted by a surface of said hammer during rearward pivoting of said hammer to cause said trigger member to be forced to said set position,
wherein said sear and sear catch are in engagement in said set positions of said hammer and trigger member and are out of engagement in said released positions of said hammer and trigger member,
a disconnector having a hook for engaging said hammer and mounted in said fire control mechanism pocket to pivot on said transverse trigger member pivot axis,
a locking member mounted in said fire control mechanism pocket to pivot on a transverse locking member pivot axis, said locking member being pivotable between a first position at which said locking member mechanically blocks said trigger member from moving to said released position and a second position at which said locking member does not mechanically block said trigger member allowing said trigger member to be moved to said released position, said locking member spring biased toward said first position and moved against said spring bias to said second position by contact from said bolt carrier during forward movement of said bolt carrier as said bolt carrier reaches a substantially in-battery position, and
a safety selector adapted mounted in said fire control mechanism pocket to pivot between safe, standard semi-automatic, and forced reset semi-automatic positions,
whereupon in said standard semi-automatic position, rearward movement of said bolt carrier causes rearward pivoting of said hammer such that said disconnector hook catches said hammer hook, at which time a user must manually release said trigger member to free said hammer from said disconnector to permit said hammer and trigger member to pivot to said set positions so that the user can pull said trigger member to fire the firearm, and
whereupon in said forced reset semi-automatic position, rearward movement of said bolt carrier causes rearward pivoting of said hammer causing said trigger member to be forced to said set position, said safety selector preventing said disconnector hook from catching said hammer hook, and thereafter when said bolt carrier reaches the substantially in-battery position the user can pull said trigger member to fire the firearm without manually releasing said trigger member.

10. The firearm of claim 9 further comprising:
a housing having a first pair of transversely aligned openings with a hammer pin therethrough and a second pair of transversely aligned openings with a trigger member pin therethrough,
said hammer mounted on said hammer pin, said trigger member and disconnector mounted on said trigger member pin.

11. The firearm of claim 10 further comprising:
said receiver having a first pair of transversely aligned assembly pin openings and a second pair of transversely aligned assembly pin openings,
said housing first pair of openings coaxial with said receiver first pair of openings and said housing second pair of openings coaxial with said receiver second pair of openings,
a first assembly pin passing through said receiver first pair of openings and through said housing first pair of openings, and
a second assembly pin passing through said receiver second pair of openings and through said housing second pair of openings.

12. The firearm of claim 10 further including a spring which biases said trigger member towards said set position.

13. The firearm of claim 12 wherein said spring is a compression spring positioned between a forward end of said trigger member and a floor of said housing.

14. A firearm trigger mechanism comprising:
a hammer having a sear catch and a hook for engaging a disconnector and adapted to be mounted in a fire control mechanism pocket of a receiver to pivot on a transverse hammer pivot axis between set and released positions, said hammer adapted to be pivoted rearward by rearward movement of a bolt carrier,
a trigger member having a sear and adapted to be mounted in the fire control mechanism pocket to pivot on a transverse trigger member pivot axis between set and released positions, said trigger member having a surface positioned to be contacted by a surface of said hammer during rearward pivoting of said hammer to cause said trigger member to be forced to said set position,
wherein said sear and sear catch are in engagement in said set positions of said hammer and trigger member and are out of engagement in said released positions of said hammer and trigger member,
a disconnector having a hook for engaging said hammer and adapted to be mounted in the fire control mechanism pocket to pivot on said transverse trigger member pivot axis,
a locking member adapted to be movably mounted in the fire control mechanism pocket, said locking member being movable between a first position at which said locking member mechanically blocks said trigger member from moving to said released position and a second position at which said locking member does not mechanically block said trigger member allowing said trigger member to be moved to said released position, said locking member spring biased toward said first position and adapted to be moved against said spring bias to said second position by contact from the bolt carrier during forward movement of the bolt carrier as the bolt carrier reaches a substantially in-battery position, and
a safety selector adapted to be mounted in the fire control mechanism pocket to pivot between safe, standard semi-automatic, and forced reset semi-automatic positions,
whereupon in said standard semi-automatic position, rearward movement of the bolt carrier causes rearward pivoting of said hammer such that said disconnector hook catches said hammer hook, at which time a user must manually release said trigger member to free said hammer from said disconnector to permit said hammer and trigger member to pivot to said set positions so that the user can pull said trigger member to fire the firearm, and whereupon in said forced reset semi-automatic position, rearward movement of the bolt carrier causes rearward pivoting of said hammer causing said trigger member to be forced to said set position, said safety selector preventing said disconnector hook from catching said hammer hook, and thereafter when the bolt carrier reaches the substantially in-battery position the user can pull said trigger member to fire the firearm without manually releasing said trigger member.

\* \* \* \* \*

UNITED STATES PATENT AND TRADEMARK OFFICE
CERTIFICATE OF CORRECTION

PATENT NO. : 11,724,003 B2
APPLICATION NO. : 18/048572
DATED : August 15, 2023
INVENTOR(S) : Mladen Thomas Strbac Page 1 of 1

It is certified that error appears in the above-identified patent and that said Letters Patent is hereby corrected as shown below:

In the Specification

Column 4, Line 52, delete:
"… and a safety selector adapted mounted in the fire control …";
Insert:
--… and a safety selector adapted to be mounted in the fire control …--.

In the Claims

Column 13, Lines 38-39, Claim 9, delete:
"… a safety selector adapted mounted in said fire control mechanism pocket to pivot between safe, standard …";
Insert:
--… a safety selector adapted to be mounted in said fire control mechanism pocket to pivot between safe, standard …--.

Signed and Sealed this
Fifth Day of December, 2023

Katherine Kelly Vidal
*Director of the United States Patent and Trademark Office*